(12) United States Patent
Alvord et al.

(10) Patent No.: US 9,226,906 B2
(45) Date of Patent: Jan. 5, 2016

(54) METHOD AND NUTRITIONAL SUPPLEMENT FOR ENHANCING WEIGHT GAIN OF A MAMMAL

(71) Applicants: Travis Kurt Alvord, Orem, UT (US); Tyler Stevens Alvord, Orem, UT (US)

(72) Inventors: Travis Kurt Alvord, Orem, UT (US); Tyler Stevens Alvord, Orem, UT (US)

(73) Assignee: Supragenix, LLC, Orem, UT (US)

( * ) Notice: Subject to any disclaimer, the term of this patent is extended or adjusted under 35 U.S.C. 154(b) by 63 days.

(21) Appl. No.: 14/026,934

(22) Filed: Sep. 13, 2013

(65) Prior Publication Data
US 2015/0079198 A1 Mar. 19, 2015

(51) Int. Cl.
| | |
|---|---|
| *A61K 36/00* | (2006.01) |
| *A61K 31/16* | (2006.01) |
| *A61K 31/355* | (2006.01) |
| *A61K 33/06* | (2006.01) |
| *A61K 31/375* | (2006.01) |
| *A23L 1/00* | (2006.01) |
| *A61K 31/164* | (2006.01) |
| *A61K 31/593* | (2006.01) |
| *A61K 33/30* | (2006.01) |
| *A61K 45/06* | (2006.01) |
| *A61K 36/28* | (2006.01) |

(52) U.S. Cl.
CPC ............... *A61K 31/164* (2013.01); *A23L 1/00* (2013.01); *A61K 31/16* (2013.01); *A61K 31/355* (2013.01); *A61K 31/375* (2013.01); *A61K 31/593* (2013.01); *A61K 33/06* (2013.01); *A61K 33/30* (2013.01); *A61K 36/00* (2013.01); *A61K 36/28* (2013.01); *A61K 45/06* (2013.01)

(58) Field of Classification Search
CPC combination set(s) only.
See application file for complete search history.

(56) References Cited

U.S. PATENT DOCUMENTS

2007/0275108 A1* 11/2007 Geesamen .................... 424/754

OTHER PUBLICATIONS

Black Hole, "Controlled Labs Black Hole from Alsupplements. com", [retrieved on Jan. 21, 2015 obtained from on-line website, http://www.a1supplements.com/Black-Hole-90-Capsules-p-16160. html].*
Wayback machine (https://web.archive.org/web/20060101000000/http://www.a1supplements.com/Black-Hole-90-Capsules-p-16160. html) (Nov. 7, 2006).*
Bauer et al., "TLC and HPLC analysis of Alkamides in Echinacea Drugs", Planta Medica 55 (1989), pp. 367-371 (1989).*

* cited by examiner

*Primary Examiner* — Ernst V Arnold
*Assistant Examiner* — Kyung Sook Chang
(74) *Attorney, Agent, or Firm* — Partners Law Group, Inc; Steve Hassid

(57) ABSTRACT

The present invention relates to a method and nutritional supplement which stimulates appetite and slows metabolism of a mammal, thereby enhancing weight gain for the mammal. The method of enhancing weight gain of the mammal comprises administering to the mammal an effective amount of at least two types of alkamide or isobutylamide compound extracted from *Echinacea* species along with an antioxidant and optionally minerals. The nutritional supplement of the present invention comprises an antioxidant and at least two types of alkamide or isobutylamide compounds derived from *Echinacea* species. Minerals such as zinc and magnesium can also be added to the nutritional supplement to provide even better effect.

10 Claims, 22 Drawing Sheets

Fig. 1

| |
|---|
| Echinacea angustifolia extracts |
|     Dodeca-2E, 4E, 8Z, 10E/Z-tetraenoic acid isobutylamides |
|     Dodeca-2E,4E-dienoic acid isobutylamide |
|     Dodeca-2E-ene-8,10-diynoic acid 2-methylbutylamide |
|     Pentadeca-2E, 9Z-diene-12, 14-diynoic acid isobutylamide |
| Echinacea purpurea extracts |
|     Dodeca-2E, 4E, 8Z, 10E/Z-tetraenoic acid isobutylamides |
|     Dodeca-2E, 4E, 8Z-trienoic acid isobutylamide |
|     Dodeca-2E, 4Z-diene-8, 10-diynoic acid isobutylamide |
| Vitamin D3 (cholecalciferol USP) |
| Zinc (zinc gluconate USP) |
| Ternary Antioxidant Blend |
|     Lecithin, ascorbic acid, mixed tocopherols |

Fig. 2

| |
|---|
| Echinacea purpurea powder |
|     Dodeca-2E, 4E, 8Z, 10E/Z-tetraenoic acid isobutylamides |
|     Dodeca-2E, 4Z-diene-8, 10-diynoic acid isobutylamide |
|     Undeca-2Z, 4E-diene-8, 10-diynoic acid isobutylamide |
| Echinacea angustifolia power |
|     Dodeca-2E, 4E, 8Z, 10E/Z-tetraenoic acid isobutylamides |
|     Undeca-2-ene-8, 10-diynoic acid isobutylamide |
|     Dodeca-2E, 4E-dienoic acid isobutylamide |
| Vitamin D3 (cholecalciferol USP) |
| Zinc (zinc gluconate USP) |
| Antioxidant System |
|     Ternary Blend of Lecithin, Vitamin C and Vitamin E |

Fig.3

| Echinacea Extracts Only |||||||||| 
|---|---|---|---|---|---|---|---|---|---|
| ID | Weight Gained (lb) | Duration (Day) | Rate | ID | Weight Gained (lb) | Duration (Day) | Rate | ID | Weight Gained (lb) | Duration (Day) |
| 8909 | 8 | 107 | 0.07 | 11370 | 5 | 78 | 0.06 | 13785 | 15 | 26 |
| 8918 | 1 | 180 | 0.01 | 11371 | 1 | 32 | 0.03 | 13789 | 13 | 162 |
| 8920 | 1 | 44 | 0.02 | 11387 | 10 | 51 | 0.20 | 13797 | 15 | 117 |
| 8943 | 4 | 39 | 0.10 | 11410 | 15 | 90 | 0.17 | 13799 | 5 | 142 |
| 8944 | 1 | 44 | 0.02 | 11413 | 3 | 63 | 0.05 | 13800 | 3 | 23 |
| 8949 | 2 | 27 | 0.07 | 11414 | 15 | 32 | 0.47 | 13823 | 10 | 33 |
| 8953 | 17 | 150 | 0.11 | 11426 | 20 | 38 | 0.53 | 13827 | 12 | 58 |
| 8955 | 12 | 148 | 0.08 | 11427 | 2 | 35 | 0.06 | 13835 | 20 | 97 |
| 8956 | 10 | 183 | 0.05 | 11437 | 6 | 2 | 3.00 | 13841 | 17 | 80 |
| 8957 | 2 | 85 | 0.02 | 11451 | 20 | 135 | 0.15 | 13846 | 15 | 85 |
| 8961 | 12 | 58 | 0.21 | 11454 | 14 | 129 | 0.11 | 13847 | 15 | 59 |
| 8963 | 4 | 150 | 0.03 | 11469 | 5 | 36 | 0.14 | 13852 | 3 | 37 |
| 8964 | 4 | 32 | 0.13 | 11484 | 5 | 121 | 0.04 | 13855 | 6 | 91 |
| 8967 | 10 | 94 | 0.11 | 11486 | 5 | 83 | 0.06 | 13870 | 4 | 177 |
| 8974 | 8 | 45 | 0.18 | 11491 | 2 | 37 | 0.05 | 13871 | 4 | 43 |
| 8981 | 15 | 102 | 0.15 | 11492 | 10 | 129 | 0.08 | 13872 | 5 | 13 |
| 8982 | 5 | 46 | 0.11 | 11504 | 15 | 147 | 0.10 | 13887 | 5 | 36 |
| 8984 | 12 | 88 | 0.14 | 11521 | 20 | 134 | 0.15 | 13888 | 15 | 35 |
| 9001 | 20 | 147 | 0.14 | 11524 | 6 | 30 | 0.20 | 13889 | 10 | 91 |
| 9002 | 7 | 44 | 0.16 | 11525 | 20 | 20 | 1.00 | 13896 | 9 | 55 |
| 9003 | 20 | 32 | 0.63 | 11529 | 40 | 155 | 0.26 | 13900 | 7 | 34 |
| 9005 | 15 | 190 | 0.08 | 11533 | 12 | 58 | 0.21 | 13910 | 8 | 12 |
| 9027 | 1 | 35 | 0.03 | 11534 | 10 | 48 | 0.21 | 13916 | 4 | 122 |
| 9029 | 20 | 64 | 0.31 | 11535 | 9 | 71 | 0.13 | 13928 | 8 | 62 |
| 9037 | 20 | 130 | 0.15 | 11548 | 2 | 70 | 0.03 | 13930 | 7 | 42 |
| 9060 | 6 | 30 | 0.20 | 11552 | 10 | 42 | 0.24 | 13936 | 20 | 33 |
| 9063 | 10 | 136 | 0.07 | 11558 | 8 | 34 | 0.24 | 13950 | 20 | 40 |
| 9086 | 5 | 59 | 0.08 | 11562 | 10 | 29 | 0.34 | 13953 | 8 | 98 |
| 9089 | 20 | 64 | 0.31 | 11563 | 5 | 152 | 0.03 | 13971 | 2 | 42 |
| 9096 | 2 | 35 | 0.06 | 11564 | 2 | 47 | 0.04 | 13977 | 12 | 68 |
| 9099 | 3 | 52 | 0.06 | 11573 | 14 | 191 | 0.07 | 13980 | 5 | 64 |
| 9100 | 1 | 29 | 0.03 | 11576 | 2 | 84 | 0.02 | 13983 | 16 | 64 |
| 9113 | 5 | 51 | 0.10 | 11594 | 10 | 90 | 0.11 | 14002 | 4 | 61 |
| 9121 | 30 | 219 | 0.14 | 11603 | 6 | 33 | 0.18 | 14004 | 8 | 114 |
| 9134 | 30 | 48 | 0.63 | 11605 | 10 | 181 | 0.06 | 14017 | 3 | 82 |
| 9136 | 2 | 35 | 0.06 | 11606 | 2 | 52 | 0.04 | 14025 | 20 | 19 |
| 9140 | 4 | 64 | 0.06 | 11611 | 2 | 12 | 0.17 | 14030 | 30 | 24 |
| 9141 | 11 | 35 | 0.31 | 11628 | 2 | 93 | 0.02 | 14050 | 1 | 77 |
| 9145 | 13 | 42 | 0.31 | 11631 | 12 | 46 | 0.26 | 14054 | 10 | 92 |
| 9160 | 10 | 33 | 0.30 | 11632 | 8 | 42 | 0.19 | 14056 | 5 | 55 |
| 9164 | 1 | 43 | 0.02 | 11634 | 18 | 150 | 0.12 | 14066 | 3 | 25 |
| 9177 | 25 | 51 | 0.49 | 11640 | 24 | 160 | 0.15 | 14068 | 5 | 77 |
| 9181 | 10 | 157 | 0.06 | 11642 | 3 | 30 | 0.10 | 14107 | 15 | 30 |
| 9183 | 1 | 43 | 0.02 | 11652 | 13 | 194 | 0.07 | 14109 | 5 | 25 |
| 9185 | 22 | 53 | 0.42 | 11655 | 30 | 188 | 0.16 | 14114 | 5 | 61 |
| 9213 | 3 | 35 | 0.09 | 11666 | 10 | 76 | 0.13 | 14115 | 11 | 43 |
| 9225 | 10 | 96 | 0.10 | 11676 | 2 | 36 | 0.06 | 14116 | 5 | 95 |
| 9239 | 25 | 32 | 0.78 | 11693 | 5 | 33 | 0.15 | 14121 | 9 | 4 |
| 9249 | 25 | 182 | 0.14 | 11696 | 4 | 34 | 0.12 | 14125 | 30 | 91 |
| 9262 | 5 | 66 | 0.08 | 11700 | 10 | 64 | 0.16 | 14140 | 10 | 38 |
| 9276 | 6 | 43 | 0.14 | 11707 | 20 | 86 | 0.23 | 14144 | 8 | 33 |
| 9283 | 5 | 83 | 0.06 | 11711 | 10 | 64 | 0.16 | 14147 | 3 | 32 |
| 9284 | 5 | 69 | 0.07 | 11713 | 20 | 19 | 1.05 | 14154 | 3 | 119 |
| 9292 | 20 | 34 | 0.59 | 11718 | 15 | 125 | 0.12 | 14155 | 10 | 23 |
| 9300 | 10 | 43 | 0.23 | 11719 | 15 | 35 | 0.43 | 14159 | 8 | 70 |

Fig.3 (continued)

| | | | | | | | | | |
|---|---|---|---|---|---|---|---|---|---|
| 9303 | 2 | 84 | 0.02 | 11730 | 15 | 197 | 0.08 | 14162 | 35 | 137 |
| 9308 | 2 | 48 | 0.04 | 11731 | 16 | 25 | 0.64 | 14167 | 5 | 96 |
| 9310 | 3 | 145 | 0.02 | 11734 | 40 | 188 | 0.21 | 14171 | 20 | 130 |
| 9311 | 8 | 89 | 0.09 | 11747 | 10 | 65 | 0.15 | 14175 | 6 | 68 |
| 9317 | 85 | 199 | 0.43 | 11754 | 5 | 114 | 0.04 | 14181 | 4 | 59 |
| 9320 | 2 | 31 | 0.06 | 11765 | 5 | 34 | 0.15 | 14192 | 12 | 83 |
| 9321 | 1 | 58 | 0.02 | 11772 | 10 | 51 | 0.20 | 14226 | 2 | 56 |
| 9329 | 15 | 24 | 0.63 | 11773 | 20 | 30 | 0.67 | 14230 | 8 | 98 |
| 9344 | 7 | 33 | 0.21 | 11785 | 20 | 63 | 0.32 | 14231 | 20 | 24 |
| 9349 | 20 | 68 | 0.29 | 11786 | 10 | 38 | 0.26 | 14232 | 160 | 75 |
| 9352 | 15 | 172 | 0.09 | 11810 | 6 | 53 | 0.11 | 14253 | 20 | 25 |
| 9361 | 35 | 92 | 0.38 | 11813 | 1 | 18 | 0.06 | 14270 | 3 | 34 |
| 9362 | 10 | 157 | 0.06 | 11814 | 5 | 38 | 0.13 | 14276 | 20 | 70 |
| 9367 | 10 | 23 | 0.43 | 11831 | 4 | 19 | 0.21 | 14278 | 10 | 93 |
| 9370 | 5 | 33 | 0.15 | 11839 | 5 | 30 | 0.17 | 14282 | 3 | 52 |
| 9383 | 5 | 32 | 0.16 | 11841 | 20 | 33 | 0.61 | 14286 | 4 | 109 |
| 9384 | 4 | 33 | 0.12 | 11842 | 15 | 132 | 0.11 | 14288 | 20 | 76 |
| 9385 | 10 | 188 | 0.05 | 11850 | 15 | 84 | 0.18 | 14290 | 5 | 24 |
| 9393 | 15 | 38 | 0.39 | 11863 | 4 | 113 | 0.04 | 14323 | 2 | 50 |
| 9397 | 3 | 50 | 0.06 | 11871 | 8 | 39 | 0.21 | 14325 | 10 | 3 |
| 9427 | 10 | 32 | 0.31 | 11872 | 20 | 12 | 1.67 | 14330 | 4 | 80 |
| 9434 | 10 | 30 | 0.33 | 11895 | 10 | 60 | 0.17 | 14338 | 10 | 143 |
| 9442 | 2 | 23 | 0.09 | 11901 | 20 | 90 | 0.22 | 14339 | 25 | 88 |
| 9448 | 30 | 103 | 0.29 | 11904 | 5 | 102 | 0.05 | 14345 | 1 | 30 |
| 9452 | 10 | 103 | 0.10 | 11921 | 2 | 32 | 0.06 | 14346 | 10 | 22 |
| 9453 | 20 | 63 | 0.32 | 11926 | 2 | 30 | 0.07 | 14350 | 12 | 31 |
| 9455 | 1 | 24 | 0.04 | 11928 | 20 | 62 | 0.32 | 14359 | 15 | 46 |
| 9459 | 12 | 66 | 0.18 | 11931 | 22 | 63 | 0.35 | 14360 | 12 | 69 |
| 9463 | 20 | 63 | 0.32 | 11932 | 6 | 27 | 0.22 | 14376 | 5 | 121 |
| 9464 | 15 | 50 | 0.30 | 11939 | 3 | 54 | 0.06 | 14381 | 10 | 116 |
| 9468 | 20 | 33 | 0.61 | 11951 | 25 | 59 | 0.42 | 14388 | 5 | 40 |
| 9470 | 15 | 122 | 0.12 | 11952 | 10 | 55 | 0.18 | 14392 | 5 | 154 |
| 9480 | 1 | 75 | 0.01 | 11957 | 20 | 135 | 0.15 | 14397 | 5 | 32 |
| 9482 | 16 | 94 | 0.17 | 11961 | 6 | 40 | 0.15 | 14399 | 3 | 18 |
| 9488 | 7 | 23 | 0.30 | 11963 | 5 | 57 | 0.09 | 14402 | 2 | 28 |
| 9489 | 20 | 209 | 0.10 | 11967 | 5 | 95 | 0.05 | 14405 | 11 | 42 |
| 9495 | 3 | 50 | 0.06 | 11976 | 25 | 22 | 1.14 | 14426 | 1 | 15 |
| 9503 | 5 | 32 | 0.16 | 11986 | 20 | 99 | 0.20 | 14428 | 15 | 21 |
| 9515 | 1.5 | 20 | 0.08 | 11988 | 10 | 64 | 0.16 | 14429 | 5 | 23 |
| 9521 | 15 | 163 | 0.09 | 11990 | 12 | 124 | 0.10 | 14438 | 5 | 81 |
| 9522 | 10 | 203 | 0.05 | 11997 | 2 | 32 | 0.06 | 14439 | 10 | 114 |
| 9532 | 5 | 35 | 0.14 | 11998 | 10 | 17 | 0.59 | 14441 | 15 | 33 |
| 9543 | 2 | 35 | 0.06 | 12011 | 20 | 87 | 0.23 | 14443 | 2 | 64 |
| 9549 | 2 | 138 | 0.01 | 12016 | 5 | 150 | 0.03 | 14456 | 25 | 112 |
| 9553 | 3 | 19 | 0.16 | 12018 | 4.6 | 11 | 0.42 | 14459 | 10 | 130 |
| 9554 | 4 | 95 | 0.04 | 12020 | 4 | 21 | 0.19 | 14462 | 20 | 119 |
| 9559 | 1 | 33 | 0.03 | 12021 | 10 | 130 | 0.08 | 14463 | 10 | 4 |
| 9562 | 2 | 63 | 0.03 | 12022 | 5 | 17 | 0.29 | 14469 | 10 | 35 |
| 9563 | 3 | 180 | 0.02 | 12027 | 5 | 148 | 0.03 | 14474 | 5 | 32 |
| 9569 | 7 | 89 | 0.08 | 12038 | 10 | 196 | 0.05 | 14476 | 20 | 58 |
| 9571 | 9 | 19 | 0.47 | 12049 | 10 | 184 | 0.05 | 14480 | 20 | 85 |
| 9576 | 1 | 33 | 0.03 | 12053 | 4 | 89 | 0.04 | 14491 | 9 | 62 |
| 9580 | 7 | 35 | 0.20 | 12055 | 12 | 51 | 0.24 | 14497 | 15 | 16 |
| 9582 | 20 | 181 | 0.11 | 12067 | 30 | 63 | 0.48 | 14508 | 5 | 59 |
| 9584 | 10 | 215 | 0.05 | 12075 | 5 | 35 | 0.14 | 14535 | 2 | 6 |
| 9595 | 10 | 62 | 0.16 | 12076 | 12 | 122 | 0.10 | 14564 | 1 | 22 |
| 9610 | 10 | 141 | 0.07 | 12077 | 7 | 50 | 0.14 | 14565 | 5 | 61 |
| 9618 | 10 | 33 | 0.30 | 12078 | 10 | 108 | 0.09 | 14571 | 20 | 38 |
| 9622 | 10 | 29 | 0.34 | 12082 | 10 | 21 | 0.48 | 14572 | 40 | 93 |
| 9623 | 2 | 33 | 0.06 | 12102 | 2 | 32 | 0.06 | 14573 | 15 | 27 |
| 9629 | 5 | 57 | 0.09 | 12120 | 10 | 68 | 0.15 | 14575 | 20 | 156 |
| 9630 | 10 | 28 | 0.36 | 12123 | 20 | 30 | 0.67 | 14589 | 3 | 34 |

Fig.3 (continued)

| | | | | | | | | | | |
|---|---|---|---|---|---|---|---|---|---|---|
| 9631 | 25 | 91 | 0.27 | 12132 | 10 | 117 | 0.09 | 14592 | 2 | 94 |
| 9637 | 7 | 55 | 0.13 | 12135 | 12 | 159 | 0.08 | 14597 | 2 | 42 |
| 9644 | 15 | 22 | 0.68 | 12136 | 8 | 151 | 0.05 | 14610 | 20 | 132 |
| 9646 | 8 | 119 | 0.07 | 12140 | 1 | 3 | 0.33 | 14628 | 6 | 32 |
| 9651 | 3 | 42 | 0.07 | 12141 | 15 | 108 | 0.14 | 14631 | 5 | 140 |
| 9652 | 20 | 47 | 0.43 | 12144 | 4 | 101 | 0.04 | 14647 | 3 | 33 |
| 9658 | 3.5 | 69 | 0.05 | 12147 | 15 | 133 | 0.11 | 14666 | 7 | 95 |
| 9672 | 4 | 98 | 0.04 | 12154 | 20 | 17 | 1.18 | 14672 | 5 | 41 |
| 9676 | 5 | 69 | 0.07 | 12158 | 1 | 99 | 0.01 | 14673 | 10 | 58 |
| 9692 | 15 | 77 | 0.19 | 12160 | 6 | 18 | 0.33 | 14684 | 20 | 103 |
| 9712 | 10 | 60 | 0.17 | 12164 | 8 | 64 | 0.13 | 14687 | 15 | 97 |
| 9725 | 4 | 69 | 0.06 | 12170 | 60 | 132 | 0.45 | 14728 | 8 | 19 |
| 9728 | 20 | 82 | 0.24 | 12171 | 30 | 131 | 0.23 | 14732 | 25 | 33 |
| 9731 | 5 | 39 | 0.13 | 12178 | 20 | 34 | 0.59 | 14752 | 4 | 128 |
| 9736 | 10 | 144 | 0.07 | 12183 | 10 | 14 | 0.71 | 14764 | 7 | 119 |
| 9739 | 2 | 30 | 0.07 | 12196 | 6 | 62 | 0.10 | 14776 | 10 | 122 |
| 9748 | 18 | 122 | 0.15 | 12200 | 5 | 15 | 0.33 | 14781 | 25 | 90 |
| 9755 | 1 | 35 | 0.03 | 12205 | 3 | 49 | 0.06 | 14794 | 10 | 157 |
| 9763 | 5 | 36 | 0.14 | 12209 | 3 | 32 | 0.09 | 14799 | 5 | 95 |
| 9765 | 2 | 28 | 0.07 | 12216 | 10 | 32 | 0.31 | 14810 | 12 | 164 |
| 9775 | 10 | 74 | 0.14 | 12221 | 4 | 34 | 0.12 | 14842 | 2 | 19 |
| 9778 | 15 | 63 | 0.24 | 12223 | 10 | 199 | 0.05 | 14857 | 2 | 67 |
| 9780 | 5 | 158 | 0.03 | 12231 | 3 | 148 | 0.02 | 14858 | 6 | 33 |
| 9784 | 10 | 33 | 0.30 | 12239 | 3 | 14 | 0.21 | 14860 | 20 | 62 |
| 9786 | 3 | 20 | 0.15 | 12242 | 5 | 36 | 0.14 | 14863 | 2 | 80 |
| 9787 | 20 | 172 | 0.12 | 12254 | 10 | 34 | 0.29 | 14865 | 1 | 129 |
| 9796 | 6 | 60 | 0.10 | 12259 | 20 | 54 | 0.37 | 14894 | 15 | 151 |
| 9800 | 15 | 130 | 0.12 | 12272 | 25 | 184 | 0.14 | 14896 | 3 | 23 |
| 9802 | 10 | 166 | 0.06 | 12276 | 20 | 32 | 0.63 | 14898 | 15 | 32 |
| 9803 | 20 | 181 | 0.11 | 12283 | 12 | 36 | 0.33 | 14909 | 5 | 87 |
| 9814 | 2 | 33 | 0.06 | 12286 | 45 | 168 | 0.27 | 14927 | 6 | 63 |
| 9818 | 3 | 32 | 0.09 | 12292 | 2 | 67 | 0.03 | 14931 | 35 | 64 |
| 9822 | 2 | 34 | 0.06 | 12298 | 6 | 159 | 0.04 | 14944 | 10 | 12 |
| 9833 | 8 | 98 | 0.08 | 12310 | 2 | 56 | 0.04 | 14952 | 25 | 60 |
| 9839 | 3 | 31 | 0.10 | 12311 | 2 | 71 | 0.03 | 14957 | 1 | 137 |
| 9844 | 6 | 36 | 0.17 | 12328 | 15 | 64 | 0.23 | 14964 | 10 | 53 |
| 9858 | 10 | 33 | 0.30 | 12333 | 15 | 85 | 0.18 | 14966 | 4 | 121 |
| 9859 | 20 | 67 | 0.30 | 12340 | 7 | 129 | 0.05 | 14969 | 10 | 30 |
| 9861 | 10 | 94 | 0.11 | 12347 | 5 | 68 | 0.07 | 14972 | 10 | 46 |
| 9894 | 10 | 95 | 0.11 | 12353 | 4 | 129 | 0.03 | 14978 | 8 | 67 |
| 9896 | 2 | 96 | 0.02 | 12358 | 10 | 140 | 0.07 | 14981 | 5 | 16 |
| 9909 | 2 | 125 | 0.02 | 12361 | 7 | 24 | 0.29 | 14987 | 10 | 66 |
| 9921 | 3 | 17 | 0.18 | 12365 | 2 | 29 | 0.07 | 14988 | 10 | 74 |
| 9924 | 1 | 35 | 0.03 | 12366 | 3 | 16 | 0.19 | 15004 | 15 | 97 |
| 9926 | 17 | 33 | 0.52 | 12368 | 25 | 58 | 0.43 | 15009 | 1 | 37 |
| 9935 | 25 | 193 | 0.13 | 12371 | 5 | 78 | 0.06 | 15016 | 10 | 63 |
| 9944 | 12 | 57 | 0.21 | 12372 | 10 | 121 | 0.08 | 15017 | 12 | 43 |
| 9947 | 7 | 120 | 0.06 | 12374 | 20 | 42 | 0.48 | 15024 | 15 | 42 |
| 9952 | 15 | 44 | 0.34 | 12380 | 2 | 124 | 0.02 | 15025 | 5 | 30 |
| 9958 | 14 | 97 | 0.14 | 12382 | 2 | 96 | 0.02 | 15029 | 5 | 22 |
| 9961 | 10 | 90 | 0.11 | 12393 | 10 | 56 | 0.18 | 15033 | 2 | 4 |
| 9962 | 9 | 36 | 0.25 | 12395 | 2 | 34 | 0.06 | 15040 | 3 | 35 |
| 9963 | 10 | 30 | 0.33 | 12399 | 5 | 182 | 0.03 | 15044 | 28 | 65 |
| 9968 | 12 | 180 | 0.07 | 12401 | 10 | 66 | 0.15 | 15049 | 6 | 94 |
| 9969 | 10 | 99 | 0.10 | 12406 | 8 | 119 | 0.07 | 15053 | 7 | 73 |
| 9972 | 10 | 97 | 0.10 | 12411 | 2 | 96 | 0.02 | 15057 | 20 | 33 |
| 9975 | 10 | 107 | 0.09 | 12412 | 3 | 60 | 0.05 | 15061 | 20 | 42 |
| 9978 | 8 | 61 | 0.13 | 12417 | 15 | 56 | 0.27 | 15065 | 15 | 14 |
| 10003 | 10 | 15 | 0.67 | 12418 | 20 | 152 | 0.13 | 15071 | 7 | 77 |
| 10004 | 5 | 76 | 0.07 | 12421 | 3 | 35 | 0.09 | 15072 | 5 | 31 |
| 10009 | 5 | 53 | 0.09 | 12430 | 10 | 54 | 0.19 | 15074 | 15 | 52 |
| 10014 | 4 | 28 | 0.14 | 12432 | 2 | 56 | 0.04 | 15081 | 15 | 35 |

Fig.3 (continued)

| | | | | | | | | | | |
|---|---|---|---|---|---|---|---|---|---|---|
| 10018 | 12 | 57 | 0.21 | 12433 | 13 | 73 | 0.18 | 15085 | 10 | 115 |
| 10028 | 20 | 65 | 0.31 | 12434 | 30 | 12 | 2.50 | 15087 | 10 | 63 |
| 10035 | 16 | 52 | 0.31 | 12441 | 2 | 76 | 0.03 | 15094 | 10 | 21 |
| 10064 | 5 | 34 | 0.15 | 12442 | 15 | 66 | 0.23 | 15103 | 10 | 61 |
| 10066 | 12 | 151 | 0.08 | 12445 | 3 | 148 | 0.02 | 15108 | 12 | 65 |
| 10076 | 2 | 22 | 0.09 | 12453 | 2 | 46 | 0.04 | 15116 | 10 | 21 |
| 10080 | 17 | 158 | 0.11 | 12465 | 25 | 39 | 0.64 | 15118 | 15 | 72 |
| 10086 | 11 | 73 | 0.15 | 12479 | 10 | 21 | 0.48 | 15121 | 20 | 31 |
| 10087 | 10 | 85 | 0.12 | 12480 | 20 | 59 | 0.34 | 15139 | 5 | 20 |
| 10089 | 6 | 83 | 0.07 | 12482 | 10 | 120 | 0.08 | 15146 | 25 | 134 |
| 10097 | 11 | 34 | 0.32 | 12483 | 20 | 15 | 1.33 | 15147 | 2 | 36 |
| 10108 | 2 | 121 | 0.02 | 12489 | 7 | 33 | 0.21 | 15151 | 35 | 117 |
| 10112 | 10 | 63 | 0.16 | 12492 | 4 | 34 | 0.12 | 15159 | 1 | 63 |
| 10117 | 10 | 56 | 0.18 | 12507 | 15 | 39 | 0.38 | 15161 | 15 | 108 |
| 10118 | 5 | 30 | 0.17 | 12514 | 3 | 5 | 0.60 | 15169 | 5 | 40 |
| 10136 | 10 | 35 | 0.29 | 12517 | 12 | 54 | 0.22 | 15175 | 30 | 120 |
| 10140 | 10 | 91 | 0.11 | 12523 | 10 | 92 | 0.11 | 15178 | 10 | 128 |
| 10146 | 10 | 62 | 0.16 | 12531 | 8 | 32 | 0.25 | 15181 | 30 | 34 |
| 10150 | 12 | 211 | 0.06 | 12534 | 6 | 67 | 0.09 | 15184 | 8 | 20 |
| 10154 | 30 | 36 | 0.83 | 12537 | 20 | 97 | 0.21 | 15192 | 2 | 7 |
| 10164 | 2 | 33 | 0.06 | 12538 | 20 | 140 | 0.14 | 15196 | 11 | 21 |
| 10173 | 2 | 27 | 0.07 | 12543 | 8 | 5 | 1.60 | 15203 | 15 | 91 |
| 10174 | 6 | 14 | 0.43 | 12552 | 6 | 34 | 0.18 | 15205 | 10 | 104 |
| 10186 | 8 | 19 | 0.42 | 12554 | 9 | 125 | 0.07 | 15209 | 12 | 84 |
| 10188 | 15 | 61 | 0.25 | 12560 | 5 | 62 | 0.08 | 15217 | 10 | 65 |
| 10204 | 15 | 41 | 0.37 | 12563 | 20 | 122 | 0.16 | 15223 | 20 | 121 |
| 10215 | 4 | 64 | 0.06 | 12570 | 2 | 26 | 0.08 | 15236 | 5 | 30 |
| 10221 | 20 | 34 | 0.59 | 12578 | 15 | 106 | 0.14 | 15257 | 25 | 138 |
| 10223 | 12 | 75 | 0.16 | 12581 | 15 | 63 | 0.24 | 15259 | 15 | 89 |
| 10224 | 10 | 35 | 0.29 | 12583 | 20 | 94 | 0.21 | 15280 | 23 | 42 |
| 10235 | 20 | 110 | 0.18 | 12587 | 11 | 63 | 0.17 | 15282 | 11 | 146 |
| 10238 | 15 | 28 | 0.54 | 12588 | 4 | 62 | 0.06 | 15283 | 20 | 12 |
| 10251 | 4 | 186 | 0.02 | 12592 | 2 | 51 | 0.04 | 15285 | 3 | 58 |
| 10253 | 3 | 14 | 0.21 | 12601 | 25 | 113 | 0.22 | 15290 | 10 | 80 |
| 10257 | 10 | 84 | 0.12 | 12606 | 12 | 154 | 0.08 | 15292 | 10 | 33 |
| 10260 | 7 | 46 | 0.15 | 12607 | 15 | 92 | 0.16 | 15303 | 10 | 13 |
| 10261 | 6 | 53 | 0.11 | 12634 | 2 | 122 | 0.02 | 15306 | 12 | 84 |
| 10262 | 2 | 157 | 0.01 | 12641 | 5 | 150 | 0.03 | 15309 | 10 | 50 |
| 10270 | 15 | 92 | 0.16 | 12643 | 30 | 27 | 1.11 | 15310 | 16 | 130 |
| 10272 | 11 | 112 | 0.10 | 12644 | 5 | 167 | 0.03 | 15312 | 5 | 122 |
| 10275 | 20 | 64 | 0.31 | 12645 | 6 | 94 | 0.06 | 15314 | 20 | 4 |
| 10291 | 12 | 96 | 0.13 | 12647 | 15 | 31 | 0.48 | 15315 | 4 | 30 |
| 10292 | 10 | 99 | 0.10 | 12650 | 20 | 143 | 0.14 | 15320 | 15 | 26 |
| 10293 | 4 | 22 | 0.18 | 12651 | 20 | 66 | 0.30 | 15322 | 4 | 119 |
| 10304 | 4 | 50 | 0.08 | 12653 | 5 | 30 | 0.17 | 15333 | 25 | 49 |
| 10310 | 8 | 25 | 0.32 | 12654 | 20 | 35 | 0.57 | 15336 | 1 | 120 |
| 10318 | 10 | 33 | 0.30 | 12658 | 15 | 33 | 0.45 | 15338 | 26 | 91 |
| 10322 | 10 | 96 | 0.10 | 12659 | 10 | 157 | 0.06 | 15345 | 10 | 15 |
| 10323 | 20 | 201 | 0.10 | 12662 | 3 | 33 | 0.09 | 15357 | 15 | 20 |
| 10324 | 5 | 93 | 0.05 | 12668 | 24 | 174 | 0.14 | 15383 | 5 | 10 |
| 10330 | 6 | 93 | 0.06 | 12703 | 1 | 104 | 0.01 | 15388 | 10 | 81 |
| 10332 | 8 | 59 | 0.14 | 12706 | 20 | 83 | 0.24 | 15394 | 2 | 29 |
| 10336 | 20 | 193 | 0.10 | 12708 | 6 | 31 | 0.19 | 15404 | 5 | 120 |
| 10339 | 10 | 36 | 0.28 | 12709 | 10 | 163 | 0.06 | 15409 | 30 | 65 |
| 10341 | 4 | 24 | 0.17 | 12714 | 1 | 3 | 0.33 | 15444 | 5 | 20 |
| 10343 | 25 | 87 | 0.29 | 12729 | 7 | 21 | 0.33 | 15449 | 2 | 9 |
| 10349 | 5 | 35 | 0.14 | 12732 | 7 | 41 | 0.17 | 15450 | 2 | 31 |
| 10350 | 14 | 209 | 0.07 | 12735 | 20 | 122 | 0.16 | 15457 | 1 | 123 |
| 10357 | 2.5 | 35 | 0.07 | 12748 | 10 | 41 | 0.24 | 15464 | 15 | 55 |
| 10366 | 20 | 35 | 0.57 | 12754 | 22 | 82 | 0.27 | 15474 | 15 | 42 |
| 10367 | 17 | 120 | 0.14 | 12758 | 5 | 68 | 0.07 | 15490 | 4 | 23 |
| 10375 | 2 | 18 | 0.11 | 12759 | 15 | 101 | 0.15 | 15492 | 20 | 60 |

Fig.3 (continued)

| | | | | | | | | | | |
|---|---|---|---|---|---|---|---|---|---|---|
| 10376 | 10 | 115 | 0.09 | 12764 | 3 | 111 | 0.03 | 15511 | 5 | 19 |
| 10377 | 2 | 22 | 0.09 | 12765 | 2 | 65 | 0.03 | 15515 | 15 | 35 |
| 10378 | 6 | 70 | 0.09 | 12770 | 7 | 18 | 0.39 | 15518 | 4 | 4 |
| 10387 | 2 | 118 | 0.02 | 12771 | 22 | 95 | 0.23 | 15524 | 20 | 116 |
| 10412 | 3 | 25 | 0.12 | 12774 | 15 | 53 | 0.28 | 15529 | 13 | 149 |
| 10414 | 2 | 19 | 0.11 | 12800 | 10 | 136 | 0.07 | 15529 | 4 | 149 |
| 10415 | 32 | 93 | 0.34 | 12821 | 10 | 94 | 0.11 | 15536 | 20 | 53 |
| 10430 | 5 | 30 | 0.17 | 12822 | 18 | 120 | 0.15 | 15538 | 2 | 45 |
| 10431 | 15 | 55 | 0.27 | 12823 | 50 | 94 | 0.53 | 15545 | 10 | 68 |
| 10450 | 7 | 26 | 0.27 | 12825 | 15 | 116 | 0.13 | 15548 | 4 | 43 |
| 10453 | 6 | 54 | 0.11 | 12850 | 5 | 151 | 0.03 | 15550 | 8 | 88 |
| 10456 | 5 | 32 | 0.16 | 12857 | 5 | 24 | 0.21 | 15553 | 6 | 94 |
| 10458 | 4 | 60 | 0.07 | 12858 | 5 | 62 | 0.08 | 15555 | 22 | 42 |
| 10463 | 20 | 16 | 1.25 | 12863 | 20 | 89 | 0.22 | 15581 | 12 | 57 |
| 10469 | 6 | 29 | 0.21 | 12877 | 20 | 37 | 0.54 | 15592 | 10 | 59 |
| 10472 | 3 | 95 | 0.03 | 12892 | 5 | 87 | 0.06 | 15596 | 12 | 61 |
| 10487 | 30 | 152 | 0.20 | 12909 | 2 | 142 | 0.01 | 15599 | 10 | 44 |
| 10490 | 15 | 51 | 0.29 | 12913 | 20 | 32 | 0.63 | 15600 | 14 | 54 |
| 10494 | 5 | 66 | 0.08 | 12914 | 6 | 58 | 0.10 | 15602 | 3 | 28 |
| 10499 | 2 | 186 | 0.01 | 12919 | 15 | 172 | 0.09 | 15603 | 5 | 142 |
| 10502 | 3 | 153 | 0.02 | 12930 | 5 | 98 | 0.05 | 15604 | 11 | 37 |
| 10503 | 5 | 11 | 0.45 | 12932 | 5 | 35 | 0.14 | 15608 | 10 | 31 |
| 10505 | 12 | 24 | 0.50 | 12935 | 1 | 122 | 0.01 | 15613 | 2 | 26 |
| 10509 | 9 | 33 | 0.27 | 12950 | 20 | 23 | 0.87 | 15617 | 20 | 75 |
| 10510 | 10 | 33 | 0.30 | 12972 | 2 | 35 | 0.06 | 15622 | 1.5 | 82 |
| 10517 | 2 | 155 | 0.01 | 12973 | 15 | 133 | 0.11 | 15631 | 20 | 52 |
| 10520 | 7 | 29 | 0.24 | 12980 | 30 | 148 | 0.20 | 15641 | 5 | 51 |
| 10523 | 10 | 47 | 0.21 | 12989 | 30 | 35 | 0.86 | 15650 | 15 | 117 |
| 10534 | 20 | 70 | 0.29 | 12990 | 2 | 11 | 0.18 | 15653 | 1 | 30 |
| 10553 | 4 | 36 | 0.11 | 12992 | 10 | 54 | 0.19 | 15658 | 8 | 39 |
| 10557 | 6.8 | 141 | 0.05 | 12995 | 15 | 63 | 0.24 | 15664 | 10 | 32 |
| 10560 | 1 | 24 | 0.04 | 13007 | 20 | 42 | 0.48 | 15670 | 13.5 | 32 |
| 10563 | 20 | 187 | 0.11 | 13009 | 10 | 103 | 0.10 | 15679 | 10 | 65 |
| 10565 | 10 | 25 | 0.40 | 13015 | 19 | 71 | 0.27 | 15686 | 7 | 54 |
| 10570 | 4 | 78 | 0.05 | 13024 | 5 | 6 | 0.83 | 15691 | 1 | 109 |
| 10573 | 15 | 46 | 0.33 | 13025 | 20 | 35 | 0.57 | 15697 | 5 | 80 |
| 10584 | 3 | 30 | 0.10 | 13034 | 2 | 87 | 0.02 | 15703 | 9 | 6 |
| 10592 | 15 | 89 | 0.17 | 13041 | 5 | 30 | 0.17 | 15706 | 15 | 63 |
| 10597 | 3 | 34 | 0.09 | 13045 | 15 | 143 | 0.10 | 15707 | 10 | 34 |
| 10619 | 10 | 84 | 0.12 | 13050 | 3 | 24 | 0.13 | 15711 | 20 | 49 |
| 10629 | 4 | 99 | 0.04 | 13054 | 20 | 15 | 1.33 | 15751 | 2 | 11 |
| 10632 | 5 | 30 | 0.17 | 13059 | 10 | 53 | 0.19 | 15762 | 17 | 130 |
| 10633 | 5 | 28 | 0.18 | 13063 | 20 | 9 | 2.22 | 15766 | 13 | 142 |
| 10640 | 25 | 64 | 0.39 | 13064 | 1 | 66 | 0.02 | 15776 | 3 | 147 |
| 10641 | 5 | 170 | 0.03 | 13081 | 10 | 15 | 0.67 | 15808 | 2 | 39 |
| 10647 | 10 | 51 | 0.20 | 13082 | 3 | 36 | 0.08 | 15822 | 3 | 50 |
| 10648 | 3 | 121 | 0.02 | 13088 | 9 | 34 | 0.26 | 15829 | 5 | 79 |
| 10649 | 3 | 33 | 0.09 | 13109 | 16 | 57 | 0.28 | 15831 | 9 | 36 |
| 10654 | 15 | 64 | 0.23 | 13115 | 10 | 34 | 0.29 | 15836 | 25 | 100 |
| 10666 | 3 | 171 | 0.02 | 13120 | 45 | 77 | 0.58 | 15841 | 2 | 62 |
| 10674 | 5 | 59 | 0.08 | 13121 | 8.5 | 28 | 0.30 | 15842 | 2 | 113 |
| 10682 | 5 | 49 | 0.10 | 13124 | 10 | 78 | 0.13 | 15851 | 15 | 36 |
| 10696 | 10 | 45 | 0.22 | 13134 | 4 | 59 | 0.07 | 15855 | 15 | 24 |
| 10702 | 3 | 21 | 0.14 | 13137 | 4 | 26 | 0.15 | 15858 | 1 | 33 |
| 10711 | 1 | 94 | 0.01 | 13155 | 30 | 61 | 0.49 | 15861 | 10 | 32 |
| 10715 | 3 | 135 | 0.02 | 13162 | 20 | 149 | 0.13 | 15867 | 4 | 16 |
| 10719 | 10 | 13 | 0.77 | 13164 | 10 | 34 | 0.29 | 15877 | 15 | 34 |
| 10728 | 10 | 148 | 0.07 | 13166 | 3 | 108 | 0.03 | 15884 | 5 | 64 |
| 10733 | 1 | 84 | 0.01 | 13169 | 20 | 74 | 0.27 | 15894 | 20 | 34 |
| 10736 | 2 | 17 | 0.12 | 13171 | 5 | 59 | 0.08 | 15900 | 2 | 160 |
| 10763 | 6 | 90 | 0.07 | 13173 | 8 | 32 | 0.25 | 15903 | 15 | 34 |
| 10764 | 5 | 35 | 0.14 | 13185 | 40 | 101 | 0.40 | 15908 | 10 | 95 |

Fig.3 (continued)

| | | | | | | | | | |
|---|---|---|---|---|---|---|---|---|---|
| 10767 | 11 | 40 | 0.28 | 13186 | 15 | 37 | 0.41 | 15919 | 20 | 151 |
| 10771 | 5 | 24 | 0.21 | 13187 | 8 | 64 | 0.13 | 15926 | 20 | 103 |
| 10797 | 20 | 82 | 0.24 | 13189 | 5 | 62 | 0.08 | 15934 | 2 | 42 |
| 10801 | 3 | 58 | 0.05 | 13207 | 10 | 6 | 1.67 | 15935 | 5 | 42 |
| 10809 | 40 | 91 | 0.44 | 13209 | 5 | 30 | 0.17 | 15939 | 2 | 143 |
| 10825 | 15 | 74 | 0.20 | 13210 | 3 | 36 | 0.08 | 15942 | 5 | 33 |
| 10839 | 2 | 33 | 0.06 | 13213 | 3 | 64 | 0.05 | 15951 | 2 | 149 |
| 10841 | 5 | 44 | 0.11 | 13217 | 20 | 35 | 0.57 | 15956 | 9 | 33 |
| 10843 | 23 | 52 | 0.44 | 13226 | 14 | 13 | 1.08 | 15975 | 4 | 26 |
| 10844 | 10 | 20 | 0.50 | 13230 | 7 | 31 | 0.23 | 15985 | 5 | 40 |
| 10845 | 7 | 35 | 0.20 | 13234 | 25 | 180 | 0.14 | 15988 | 1 | 21 |
| 10853 | 15 | 77 | 0.19 | 13241 | 4 | 40 | 0.10 | 15989 | 30 | 92 |
| 10858 | 9 | 147 | 0.06 | 13247 | 11 | 20 | 0.55 | 15994 | 5 | 69 |
| 10865 | 25 | 60 | 0.42 | 13254 | 10 | 14 | 0.71 | 15999 | 3 | 107 |
| 10874 | 9 | 60 | 0.15 | 13258 | 2 | 91 | 0.02 | 16005 | 10 | 68 |
| 10879 | 15 | 121 | 0.12 | 13273 | 9 | 68 | 0.13 | 16016 | 10 | 58 |
| 10891 | 10 | 32 | 0.31 | 13281 | 7 | 37 | 0.19 | 16017 | 15 | 97 |
| 10896 | 3 | 35 | 0.09 | 13283 | 10 | 68 | 0.15 | 16018 | 18 | 25 |
| 10898 | 6 | 68 | 0.09 | 13285 | 7 | 26 | 0.27 | 16026 | 14 | 50 |
| 10901 | 15 | 63 | 0.24 | 13302 | 5 | 32 | 0.16 | 16032 | 20 | 76 |
| 10904 | 15 | 145 | 0.10 | 13304 | 25 | 132 | 0.19 | 16041 | 2 | 8 |
| 10908 | 15 | 119 | 0.13 | 13305 | 15 | 36 | 0.42 | 16064 | 15 | 31 |
| 10911 | 7 | 32 | 0.22 | 13309 | 1 | 71 | 0.01 | 16071 | 10 | 82 |
| 10912 | 10 | 14 | 0.71 | 13312 | 20 | 87 | 0.23 | 16076 | 3 | 60 |
| 10929 | 18 | 78 | 0.23 | 13329 | 15 | 63 | 0.24 | 16079 | 15 | 151 |
| 10934 | 10 | 32 | 0.31 | 13330 | 20 | 6 | 3.33 | 16094 | 10 | 32 |
| 10941 | 14 | 172 | 0.08 | 13339 | 20 | 85 | 0.24 | 16097 | 15 | 118 |
| 10958 | 20 | 11 | 1.82 | 13345 | 15.5 | 36 | 0.43 | 16109 | 7 | 151 |
| 10962 | 6 | 18 | 0.33 | 13351 | 20 | 57 | 0.35 | 16115 | 15 | 35 |
| 10965 | 15 | 62 | 0.24 | 13353 | 2 | 124 | 0.02 | 16116 | 2 | 26 |
| 10970 | 5 | 90 | 0.06 | 13361 | 3 | 12 | 0.25 | 16123 | 3 | 123 |
| 10981 | 2 | 49 | 0.04 | 13363 | 20 | 18 | 1.11 | 16128 | 10 | 64 |
| 10991 | 5 | 150 | 0.03 | 13369 | 10 | 35 | 0.29 | 16132 | 40 | 109 |
| 10993 | 2 | 63 | 0.03 | 13375 | 2 | 32 | 0.06 | 16133 | 14 | 91 |
| 11004 | 12 | 34 | 0.35 | 13406 | 8 | 33 | 0.24 | 16141 | 9 | 31 |
| 11008 | 15 | 5 | 3.00 | 13409 | 9 | 43 | 0.21 | 16143 | 10 | 68 |
| 11009 | 50 | 167 | 0.30 | 13413 | 15 | 166 | 0.09 | 16157 | 12 | 119 |
| 11015 | 3 | 89 | 0.03 | 13424 | 5 | 24 | 0.21 | 16159 | 12 | 13 |
| 11017 | 16 | 33 | 0.48 | 13427 | 10 | 93 | 0.11 | 16162 | 5 | 53 |
| 11047 | 6 | 75 | 0.08 | 13432 | 1 | 19 | 0.05 | 16165 | 20 | 32 |
| 11059 | 4 | 150 | 0.03 | 13440 | 5 | 26 | 0.19 | 16166 | 12 | 60 |
| 11061 | 3 | 33 | 0.09 | 13456 | 20 | 46 | 0.43 | 16191 | 1 | 18 |
| 11066 | 5 | 46 | 0.11 | 13458 | 5 | 128 | 0.04 | 16193 | 15 | 69 |
| 11073 | 30 | 40 | 0.75 | 13471 | 10 | 32 | 0.31 | 16197 | 4 | 29 |
| 11074 | 4 | 26 | 0.15 | 13472 | 15 | 97 | 0.15 | 16202 | 20 | 34 |
| 11083 | 8 | 33 | 0.24 | 13475 | 10 | 21 | 0.48 | 16205 | 11 | 32 |
| 11100 | 1.5 | 76 | 0.02 | 13477 | 10 | 74 | 0.14 | 16207 | 3 | 79 |
| 11105 | 3 | 5 | 0.60 | 13485 | 3 | 25 | 0.12 | 16215 | 15 | 84 |
| 11113 | 15 | 85 | 0.18 | 13486 | 18 | 163 | 0.11 | 16219 | 5 | 34 |
| 11119 | 43 | 95 | 0.45 | 13487 | 10 | 69 | 0.14 | 16228 | 4 | 34 |
| 11122 | 6 | 35 | 0.17 | 13488 | 4 | 32 | 0.13 | 16231 | 3 | 63 |
| 11126 | 3 | 25 | 0.12 | 13491 | 10 | 28 | 0.36 | 16233 | 9 | 56 |
| 11136 | 2 | 142 | 0.01 | 13498 | 5 | 60 | 0.08 | 16241 | 2 | 90 |
| 11147 | 7 | 60 | 0.12 | 13499 | 4 | 147 | 0.03 | 16248 | 4 | 88 |
| 11150 | 15 | 29 | 0.52 | 13503 | 5 | 120 | 0.04 | 16250 | 6 | 23 |
| 11151 | 5 | 5 | 1.00 | 13504 | 18 | 83 | 0.22 | 16251 | 11 | 35 |
| 11157 | 30 | 123 | 0.24 | 13505 | 2 | 65 | 0.03 | 16252 | 12 | 56 |
| 11159 | 1 | 36 | 0.03 | 13506 | 11 | 27 | 0.41 | 16257 | 10 | 5 |
| 11162 | 8 | 169 | 0.05 | 13509 | 5 | 56 | 0.09 | 16270 | 2 | 31 |
| 11163 | 2 | 11 | 0.18 | 13511 | 10 | 41 | 0.24 | 16273 | 4 | 95 |
| 11166 | 10 | 5 | 2.00 | 13515 | 15 | 94 | 0.16 | 16276 | 4 | 35 |
| 11180 | 5 | 31 | 0.16 | 13518 | 1 | 5 | 0.20 | 16286 | 5 | 33 |

Fig.3 (continued)

| | | | | | | | | | | |
|---|---|---|---|---|---|---|---|---|---|---|
| 11185 | 2 | 59 | 0.03 | 13523 | 10 | 146 | 0.07 | 16297 | 5 | 80 |
| 11190 | 20 | 181 | 0.11 | 13526 | 10 | 134 | 0.07 | 16298 | 10 | 21 |
| 11192 | 4 | 15 | 0.27 | 13531 | 15 | 84 | 0.18 | 16306 | 2 | 26 |
| 11199 | 2 | 73 | 0.03 | 13534 | 10 | 28 | 0.36 | 16311 | 3 | 73 |
| 11202 | 10 | 11 | 0.91 | 13536 | 2 | 68 | 0.03 | 16332 | 27 | 61 |
| 11204 | 20 | 53 | 0.38 | 13540 | 15 | 100 | 0.15 | 16341 | 10 | 42 |
| 11212 | 10 | 75 | 0.13 | 13548 | 10 | 40 | 0.25 | 16342 | 8 | 46 |
| 11213 | 2 | 32 | 0.06 | 13566 | 10 | 72 | 0.14 | 16353 | 5 | 90 |
| 11216 | 5 | 35 | 0.14 | 13568 | 8 | 103 | 0.08 | 16361 | 12 | 35 |
| 11218 | 5 | 55 | 0.09 | 13569 | 8 | 31 | 0.26 | 16363 | 12 | 33 |
| 11220 | 17 | 93 | 0.18 | 13579 | 8 | 10 | 0.80 | 16364 | 2 | 40 |
| 11225 | 12 | 26 | 0.46 | 13589 | 2 | 17 | 0.12 | 16379 | 20 | 155 |
| 11233 | 15 | 64 | 0.23 | 13593 | 41 | 94 | 0.44 | 16380 | 7 | 29 |
| 11235 | 2 | 28 | 0.07 | 13607 | 6 | 58 | 0.10 | 16383 | 1 | 33 |
| 11251 | 10 | 13 | 0.77 | 13617 | 15 | 119 | 0.13 | 16386 | 5 | 23 |
| 11252 | 6 | 12 | 0.50 | 13623 | 3 | 129 | 0.02 | 16389 | 5 | 68 |
| 11257 | 40 | 93 | 0.43 | 13626 | 5 | 68 | 0.07 | 16390 | 10 | 117 |
| 11263 | 6 | 131 | 0.05 | 13634 | 10 | 53 | 0.19 | 16392 | 10 | 118 |
| 11265 | 10 | 12 | 0.83 | 13663 | 25 | 13 | 1.92 | 16401 | 12 | 72 |
| 11267 | 6 | 36 | 0.17 | 13673 | 10 | 87 | 0.11 | 16426 | 5 | 16 |
| 11268 | 5 | 28 | 0.18 | 13678 | 11 | 148 | 0.07 | 16429 | 3 | 51 |
| 11273 | 7 | 32 | 0.22 | 13681 | 20 | 32 | 0.63 | 16430 | 25 | 108 |
| 11275 | 10 | 46 | 0.22 | 13687 | 15 | 109 | 0.14 | 16431 | 15 | 41 |
| 11286 | 8 | 62 | 0.13 | 13690 | 17 | 102 | 0.17 | 16435 | 14 | 138 |
| 11291 | 9 | 14 | 0.64 | 13693 | 15 | 36 | 0.42 | 16440 | 10 | 84 |
| 11294 | 20 | 183 | 0.11 | 13695 | 2 | 27 | 0.07 | 16441 | 30 | 65 |
| 11304 | 10 | 88 | 0.11 | 13703 | 40 | 93 | 0.43 | 16447 | 20 | 30 |
| 11305 | 15 | 150 | 0.10 | 13712 | 5 | 21 | 0.24 | 16454 | 10 | 33 |
| 11313 | 12 | 19 | 0.63 | 13713 | 25 | 82 | 0.30 | 16466 | 10 | 21 |
| 11314 | 5 | 109 | 0.05 | 13722 | 2 | 124 | 0.02 | 16504 | 1 | 15 |
| 11323 | 3 | 35 | 0.09 | 13735 | 13 | 33 | 0.39 | 16507 | 25 | 66 |
| 11325 | 8 | 165 | 0.05 | 13742 | 20 | 91 | 0.22 | 16517 | 8 | 27 |
| 11328 | 8 | 84 | 0.10 | 13750 | 8 | 124 | 0.06 | 16522 | 3 | 33 |
| 11330 | 3 | 36 | 0.08 | 13751 | 15 | 146 | 0.10 | 16523 | 20 | 85 |
| 11340 | 15 | 90 | 0.17 | 13759 | 15 | 159 | 0.09 | 16525 | 15 | 54 |
| 11343 | 23 | 193 | 0.12 | 13760 | 10 | 31 | 0.32 | 16542 | 20 | 66 |
| 11344 | 6.5 | 27 | 0.24 | 13766 | 5 | 80 | 0.06 | 16545 | 7 | 32 |
| 11367 | 15 | 46 | 0.33 | 13767 | 5 | 33 | 0.15 | 16548 | 1 | 27 |

Fig. 4

| Echinacea Extracts with Zinc, Vitamin D3 and Ternary Blend (Lecithin, Vitamin C and Vitamin E) | | | | | | | | | |
|---|---|---|---|---|---|---|---|---|---|
| ID | Weight Gained (lb) | Duration (Day) | Rate | ID | Weight Gained (lb) | Duration (Day) | Rate | ID | Weight Gained (lb) | Duration (Day) |
| 21177 | 2 | 16 | 0.13 | 24106 | 4 | 32 | 0.13 | 27661 | 20 | 40 |
| 21179 | 6 | 32 | 0.19 | 24117 | 1 | 30 | 0.03 | 27662 | 20 | 62 |
| 21189 | 10 | 36 | 0.28 | 24118 | 13 | 36 | 0.36 | 27696 | 6 | 42 |
| 21191 | 15 | 34 | 0.44 | 24120 | 12 | 88 | 0.14 | 27702 | 9 | 61 |
| 21199 | 16 | 24 | 0.67 | 24141 | 12 | 58 | 0.21 | 27706 | 20 | 21 |
| 21211 | 1 | 90 | 0.01 | 24161 | 6 | 26 | 0.23 | 27713 | 10 | 35 |
| 21224 | 5 | 69 | 0.07 | 24176 | 7 | 31 | 0.23 | 27714 | 5 | 33 |
| 21239 | 2 | 13 | 0.15 | 24179 | 10 | 85 | 0.12 | 27716 | 20 | 62 |
| 21267 | 5.5 | 43 | 0.13 | 24195 | 7 | 32 | 0.22 | 27717 | 10 | 32 |
| 21281 | 2 | 60 | 0.03 | 24207 | 6 | 33 | 0.18 | 27720 | 30 | 26 |
| 21285 | 15 | 68 | 0.22 | 24209 | 10 | 37 | 0.27 | 27727 | 2 | 60 |
| 21286 | 15 | 112 | 0.13 | 24227 | 15 | 61 | 0.25 | 27731 | 3 | 30 |
| 21298 | 20 | 48 | 0.42 | 24230 | 8 | 4 | 2.00 | 27733 | 15 | 30 |
| 21305 | 20 | 35 | 0.57 | 24239 | 15 | 60 | 0.25 | 27749 | 6 | 24 |
| 21308 | 15 | 62 | 0.24 | 24243 | 7 | 64 | 0.11 | 27752 | 10 | 41 |
| 21344 | 15 | 13 | 1.15 | 24254 | 5 | 58 | 0.09 | 27789 | 10 | 32 |
| 21347 | 5 | 35 | 0.14 | 24261 | 4 | 37 | 0.11 | 27796 | 5 | 53 |
| 21352 | 20 | 88 | 0.23 | 24293 | 5 | 68 | 0.07 | 27797 | 10 | 58 |
| 21355 | 30 | 91 | 0.33 | 24323 | 4 | 21 | 0.19 | 27803 | 2 | 24 |
| 21372 | 6 | 62 | 0.10 | 24326 | 3 | 14 | 0.21 | 27813 | 15 | 67 |
| 21384 | 5 | 70 | 0.07 | 24329 | 8 | 31 | 0.26 | 27818 | 2 | 26 |
| 21391 | 15 | 50 | 0.30 | 24332 | 18 | 4 | 4.50 | 27823 | 5 | 55 |
| 21412 | 2 | 59 | 0.03 | 24333 | 20 | 35 | 0.57 | 27824 | 5 | 58 |
| 21421 | 20 | 33 | 0.61 | 24346 | 10 | 30 | 0.33 | 27825 | 15 | 51 |
| 21431 | 10 | 63 | 0.16 | 24376 | 30 | 20 | 1.50 | 27834 | 1 | 54 |
| 21434 | 10 | 44 | 0.23 | 24406 | 5 | 44 | 0.11 | 27839 | 3 | 18 |
| 21438 | 20 | 30 | 0.67 | 24408 | 7 | 34 | 0.21 | 27846 | 5 | 4 |
| 21439 | 20 | 41 | 0.49 | 24413 | 17 | 13 | 1.31 | 27872 | 12 | 37 |
| 21440 | 6 | 4 | 1.50 | 24422 | 3 | 14 | 0.21 | 27885 | 12 | 47 |
| 21467 | 5 | 22 | 0.23 | 24431 | 5 | 76 | 0.07 | 27903 | 7 | 30 |
| 21475 | 9 | 63 | 0.14 | 24457 | 15 | 44 | 0.34 | 27905 | 10 | 33 |
| 21486 | 5 | 32 | 0.16 | 24460 | 10 | 61 | 0.16 | 27906 | 6 | 58 |
| 21498 | 9 | 33 | 0.27 | 24470 | 1 | 30 | 0.03 | 27924 | 2 | 21 |

Fig.4 (continued)

| | | | | | | | | | |
|---|---|---|---|---|---|---|---|---|---|
| 21501 | 9 | 15 | 0.60 | 24479 | 5 | 8 | 0.63 | 27933 | 10 | 13 |
| 21508 | 23 | 80 | 0.29 | 24489 | 2 | 27 | 0.07 | 27940 | 7 | 24 |
| 21510 | 7 | 49 | 0.14 | 24509 | 5 | 65 | 0.08 | 27959 | 2 | 30 |
| 21522 | 20 | 42 | 0.48 | 24516 | 3 | 33 | 0.09 | 27981 | 18 | 21 |
| 21525 | 20 | 30 | 0.67 | 24523 | 17 | 47 | 0.36 | 27985 | 1 | 29 |
| 21539 | 10 | 55 | 0.18 | 24540 | 6 | 28 | 0.21 | 27991 | 12 | 45 |
| 21545 | 4 | 76 | 0.05 | 24542 | 5 | 37 | 0.14 | 28006 | 35 | 59 |
| 21548 | 7 | 85 | 0.08 | 24546 | 20 | 54 | 0.37 | 28023 | 5 | 33 |
| 21553 | 22 | 39 | 0.56 | 24558 | 10 | 63 | 0.16 | 28035 | 5 | 30 |
| 21566 | 7 | 99 | 0.07 | 24573 | 10 | 48 | 0.21 | 28050 | 10 | 63 |
| 21569 | 2 | 29 | 0.07 | 24591 | 5 | 81 | 0.06 | 28051 | 10 | 32 |
| 21584 | 10 | 37 | 0.27 | 24599 | 15 | 55 | 0.27 | 28062 | 9 | 43 |
| 21588 | 5 | 78 | 0.06 | 24608 | 10 | 40 | 0.25 | 28067 | 10 | 33 |
| 21590 | 2 | 32 | 0.06 | 24613 | 15 | 32 | 0.47 | 28094 | 10 | 62 |
| 21622 | 21 | 47 | 0.45 | 24625 | 2 | 32 | 0.06 | 28097 | 7 | 25 |
| 21629 | 7 | 32 | 0.22 | 24635 | 10 | 5 | 2.00 | 28113 | 10 | 44 |
| 21637 | 7 | 36 | 0.19 | 24644 | 9 | 85 | 0.11 | 28126 | 7 | 30 |
| 21641 | 15 | 62 | 0.24 | 24655 | 5 | 33 | 0.15 | 28144 | 5 | 54 |
| 21648 | 3 | 26 | 0.12 | 24666 | 4 | 38 | 0.11 | 28158 | 10 | 40 |
| 21649 | 15 | 106 | 0.14 | 24670 | 3 | 84 | 0.04 | 28165 | 5 | 64 |
| 21654 | 5 | 47 | 0.11 | 24671 | 10 | 47 | 0.21 | 28173 | 5 | 47 |
| 21659 | 11 | 29 | 0.38 | 24683 | 4 | 36 | 0.11 | 28183 | 5 | 27 |
| 21664 | 4 | 50 | 0.08 | 24686 | 8 | 38 | 0.21 | 28244 | 2 | 29 |
| 21671 | 3 | 15 | 0.20 | 24689 | 15 | 44 | 0.34 | 28246 | 10 | 32 |
| 21676 | 4 | 100 | 0.04 | 24694 | 3 | 11 | 0.27 | 28249 | 7 | 36 |
| 21678 | 3 | 27 | 0.11 | 24699 | 5 | 62 | 0.08 | 28251 | 8 | 23 |
| 21684 | 10 | 21 | 0.48 | 24704 | 3 | 65 | 0.05 | 28260 | 5 | 35 |
| 21688 | 5 | 8 | 0.63 | 24708 | 2 | 45 | 0.04 | 28283 | 12 | 59 |
| 21689 | 15 | 47 | 0.32 | 24713 | 4 | 47 | 0.09 | 28287 | 15 | 51 |
| 21691 | 2 | 108 | 0.02 | 24716 | 11 | 56 | 0.20 | 28288 | 1 | 26 |
| 21709 | 1 | 15 | 0.07 | 24728 | 17 | 35 | 0.49 | 28294 | 10 | 30 |
| 21718 | 6 | 57 | 0.11 | 24734 | 10 | 63 | 0.16 | 28301 | 15 | 63 |
| 21724 | 20 | 28 | 0.71 | 24742 | 5 | 31 | 0.16 | 28306 | 2 | 24 |
| 21727 | 5 | 31 | 0.16 | 24743 | 20 | 32 | 0.63 | 28323 | 10 | 63 |
| 21741 | 6 | 73 | 0.08 | 24744 | 2 | 86 | 0.02 | 28325 | 3 | 31 |
| 21747 | 3 | 33 | 0.09 | 24751 | 25 | 13 | 1.92 | 28336 | 5 | 48 |
| 21756 | 20 | 32 | 0.63 | 24752 | 2 | 59 | 0.03 | 28337 | 2 | 24 |
| 21772 | 5 | 45 | 0.11 | 24757 | 2 | 53 | 0.04 | 28341 | 16 | 52 |
| 21774 | 2 | 48 | 0.04 | 24763 | 10 | 49 | 0.20 | 28345 | 3 | 48 |

Fig.4 (continued)

| 21780 | 2 | 8 | 0.25 | 24764 | 20 | 62 | 0.32 | 28403 | 1 | 2 |
|---|---|---|---|---|---|---|---|---|---|---|
| 21782 | 7 | 40 | 0.18 | 24768 | 20 | 21 | 0.95 | 28408 | 20 | 29 |
| 21786 | 5 | 31 | 0.16 | 24777 | 5 | 49 | 0.10 | 28419 | 10 | 63 |
| 21790 | 11 | 18 | 0.61 | 24790 | 5 | 33 | 0.15 | 28421 | 5 | 57 |
| 21795 | 12 | 61 | 0.20 | 24791 | 25 | 56 | 0.45 | 28427 | 2 | 31 |
| 21811 | 8 | 97 | 0.08 | 24795 | 3 | 10 | 0.30 | 28475 | 5 | 67 |
| 21819 | 10 | 40 | 0.25 | 24796 | 5 | 26 | 0.19 | 28504 | 20 | 45 |
| 21823 | 5 | 36 | 0.14 | 24802 | 4 | 34 | 0.12 | 28511 | 9 | 60 |
| 21824 | 10 | 41 | 0.24 | 24827 | 40 | 74 | 0.54 | 28514 | 10 | 32 |
| 21832 | 10 | 92 | 0.11 | 24829 | 10 | 53 | 0.19 | 28527 | 7 | 18 |
| 21837 | 5 | 61 | 0.08 | 24830 | 20 | 75 | 0.27 | 28547 | 5 | 35 |
| 21854 | 12 | 103 | 0.12 | 24834 | 6 | 42 | 0.14 | 28550 | 10 | 32 |
| 21857 | 7 | 56 | 0.13 | 24849 | 4 | 45 | 0.09 | 28553 | 1 | 6 |
| 21860 | 10 | 30 | 0.33 | 24855 | 5 | 67 | 0.07 | 28565 | 4 | 30 |
| 21871 | 30 | 33 | 0.91 | 24867 | 15 | 62 | 0.24 | 28566 | 10 | 56 |
| 21881 | 4 | 42 | 0.10 | 24881 | 8 | 58 | 0.14 | 28578 | 3 | 30 |
| 21882 | 5 | 62 | 0.08 | 24882 | 10 | 30 | 0.33 | 28587 | 9 | 21 |
| 21885 | 5 | 60 | 0.08 | 24900 | 2 | 34 | 0.06 | 28599 | 20 | 33 |
| 21888 | 6 | 37 | 0.16 | 24918 | 5 | 45 | 0.11 | 28603 | 5 | 20 |
| 21893 | 10 | 70 | 0.14 | 24923 | 4 | 33 | 0.12 | 28604 | 10 | 9 |
| 21901 | 2 | 53 | 0.04 | 24942 | 2 | 36 | 0.06 | 28608 | 7 | 41 |
| 21905 | 3 | 85 | 0.04 | 24965 | 9 | 32 | 0.28 | 28610 | 9 | 57 |
| 21919 | 15 | 53 | 0.28 | 24968 | 3 | 32 | 0.09 | 28617 | 10 | 26 |
| 21923 | 4 | 21 | 0.19 | 24977 | 20 | 30 | 0.67 | 28631 | 15 | 66 |
| 21930 | 15 | 47 | 0.32 | 24989 | 2 | 31 | 0.06 | 28634 | 5 | 20 |
| 21934 | 15 | 80 | 0.19 | 24994 | 40 | 27 | 1.48 | 28636 | 15 | 44 |
| 21945 | 20 | 52 | 0.38 | 25002 | 10 | 25 | 0.40 | 28640 | 5 | 62 |
| 21949 | 1 | 24 | 0.04 | 25008 | 7 | 63 | 0.11 | 28646 | 10 | 63 |
| 21957 | 20 | 90 | 0.22 | 25059 | 10 | 34 | 0.29 | 28649 | 7 | 30 |
| 21975 | 8 | 68 | 0.12 | 25072 | 10 | 39 | 0.26 | 28653 | 5 | 29 |
| 21977 | 20 | 42 | 0.48 | 25086 | 4 | 29 | 0.14 | 28656 | 2 | 18 |
| 21981 | 11 | 83 | 0.13 | 25108 | 2 | 74 | 0.03 | 28658 | 4 | 43 |
| 21982 | 5 | 25 | 0.20 | 25117 | 22 | 33 | 0.67 | 28665 | 3 | 33 |
| 21988 | 4 | 26 | 0.15 | 25123 | 1 | 18 | 0.06 | 28669 | 2 | 20 |
| 21997 | 18 | 44 | 0.41 | 25132 | 12 | 48 | 0.25 | 28690 | 4 | 32 |
| 22009 | 20 | 12 | 1.67 | 25139 | 10 | 35 | 0.29 | 28693 | 3 | 28 |
| 22014 | 10 | 33 | 0.30 | 25148 | 2 | 36 | 0.06 | 28694 | 10 | 44 |
| 22017 | 10 | 54 | 0.19 | 25152 | 15 | 62 | 0.24 | 28696 | 3 | 19 |
| 22032 | 3 | 72 | 0.04 | 25154 | 3 | 13 | 0.23 | 28699 | 20 | 15 |

Fig.4 (continued)

| | | | | | | | | | |
|---|---|---|---|---|---|---|---|---|---|
| 22034 | 10 | 82 | 0.12 | 25168 | 8 | 64 | 0.13 | 28713 | 4 | 20 |
| 22042 | 5 | 59 | 0.08 | 25177 | 4 | 45 | 0.09 | 28722 | 5 | 34 |
| 22049 | 20 | 65 | 0.31 | 25209 | 10 | 78 | 0.13 | 28723 | 10 | 52 |
| 22055 | 1 | 37 | 0.03 | 25216 | 30 | 47 | 0.64 | 28737 | 5 | 35 |
| 22057 | 1 | 19 | 0.05 | 25219 | 5 | 35 | 0.14 | 28744 | 4 | 58 |
| 22067 | 10 | 32 | 0.31 | 25222 | 15 | 65 | 0.23 | 28747 | 10 | 56 |
| 22078 | 20 | 5 | 4.00 | 25241 | 10 | 57 | 0.18 | 28757 | 12 | 33 |
| 22088 | 4 | 55 | 0.07 | 25243 | 10 | 35 | 0.29 | 28772 | 5 | 27 |
| 22112 | 30 | 51 | 0.59 | 25252 | 10 | 26 | 0.38 | 28774 | 5 | 24 |
| 22143 | 10 | 65 | 0.15 | 25258 | 5 | 16 | 0.31 | 28792 | 3 | 29 |
| 22149 | 2 | 29 | 0.07 | 25266 | 10 | 56 | 0.18 | 28795 | 1 | 44 |
| 22158 | 10 | 101 | 0.10 | 25267 | 10 | 62 | 0.16 | 28798 | 5 | 41 |
| 22167 | 20 | 90 | 0.22 | 25273 | 5 | 33 | 0.15 | 28810 | 5 | 31 |
| 22176 | 3 | 33 | 0.09 | 25290 | 20 | 30 | 0.67 | 28818 | 2 | 60 |
| 22180 | 20 | 30 | 0.67 | 25291 | 2 | 27 | 0.07 | 28820 | 3 | 21 |
| 22181 | 20 | 22 | 0.91 | 25292 | 6 | 50 | 0.12 | 28821 | 1 | 13 |
| 22190 | 10 | 54 | 0.19 | 25308 | 8 | 31 | 0.26 | 28825 | 6 | 23 |
| 22196 | 5 | 85 | 0.06 | 25316 | 20 | 72 | 0.28 | 28841 | 2 | 16 |
| 22210 | 10 | 33 | 0.30 | 25317 | 6 | 33 | 0.18 | 28875 | 6 | 35 |
| 22215 | 8 | 32 | 0.25 | 25321 | 1 | 32 | 0.03 | 28905 | 22 | 61 |
| 22218 | 10 | 94 | 0.11 | 25327 | 8 | 63 | 0.13 | 28919 | 2 | 37 |
| 22224 | 20 | 69 | 0.29 | 25330 | 3 | 49 | 0.06 | 28922 | 5 | 30 |
| 22225 | 20 | 46 | 0.43 | 25332 | 5 | 26 | 0.19 | 28926 | 6 | 63 |
| 22228 | 3 | 6 | 0.50 | 25334 | 5 | 31 | 0.16 | 28932 | 12 | 55 |
| 22231 | 10 | 68 | 0.15 | 25335 | 5 | 24 | 0.21 | 28935 | 10 | 33 |
| 22233 | 10 | 60 | 0.17 | 25342 | 5 | 62 | 0.08 | 28937 | 15 | 51 |
| 22240 | 6 | 65 | 0.09 | 25353 | 8 | 28 | 0.29 | 28953 | 1 | 12 |
| 22247 | 5 | 57 | 0.09 | 25379 | 10 | 36 | 0.28 | 28956 | 2 | 23 |
| 22259 | 1 | 17 | 0.06 | 25385 | 1 | 27 | 0.04 | 28960 | 8 | 35 |
| 22269 | 12 | 22 | 0.55 | 25392 | 8 | 34 | 0.24 | 28963 | 7 | 60 |
| 22277 | 3 | 99 | 0.03 | 25404 | 5 | 42 | 0.12 | 28966 | 6 | 61 |
| 22278 | 15 | 39 | 0.38 | 25412 | 10 | 52 | 0.19 | 28969 | 9 | 59 |
| 22279 | 11 | 85 | 0.13 | 25420 | 10 | 69 | 0.14 | 28972 | 2 | 36 |
| 22283 | 5 | 33 | 0.15 | 25435 | 5 | 23 | 0.22 | 28974 | 5 | 19 |
| 22284 | 15 | 102 | 0.15 | 25446 | 7 | 32 | 0.22 | 28979 | 4 | 27 |
| 22292 | 1 | 63 | 0.02 | 25453 | 4 | 33 | 0.12 | 29002 | 2 | 57 |
| 22304 | 6 | 31 | 0.19 | 25467 | 5 | 37 | 0.14 | 29015 | 4 | 11 |
| 22311 | 12 | 54 | 0.22 | 25470 | 2 | 30 | 0.07 | 29027 | 5 | 21 |
| 22313 | 2 | 58 | 0.03 | 25471 | 10 | 36 | 0.28 | 29028 | 10 | 30 |

Fig.4 (continued)

| | | | | | | | | | |
|---|---|---|---|---|---|---|---|---|---|
| 22319 | 25 | 65 | 0.38 | 25488 | 3 | 34 | 0.09 | 29042 | 6 | 59 |
| 22323 | 3 | 8 | 0.38 | 25508 | 7 | 62 | 0.11 | 29044 | 1 | 24 |
| 22324 | 8 | 20 | 0.40 | 25512 | 2 | 13 | 0.15 | 29046 | 3 | 18 |
| 22326 | 5 | 44 | 0.11 | 25519 | 8 | 33 | 0.24 | 29047 | 9 | 16 |
| 22333 | 2 | 21 | 0.10 | 25522 | 10 | 63 | 0.16 | 29049 | 10 | 64 |
| 22336 | 10 | 78 | 0.13 | 25526 | 2 | 49 | 0.04 | 29050 | 2 | 63 |
| 22342 | 4 | 90 | 0.04 | 25541 | 10 | 75 | 0.13 | 29065 | 4 | 61 |
| 22349 | 3 | 32 | 0.09 | 25542 | 2 | 15 | 0.13 | 29093 | 1 | 19 |
| 22350 | 2 | 23 | 0.09 | 25543 | 5 | 63 | 0.08 | 29143 | 10 | 36 |
| 22362 | 5 | 26 | 0.19 | 25549 | 10 | 33 | 0.30 | 29167 | 5 | 29 |
| 22363 | 15 | 35 | 0.43 | 25556 | 5 | 55 | 0.09 | 29171 | 20 | 44 |
| 22368 | 10 | 35 | 0.29 | 25560 | 4 | 65 | 0.06 | 29174 | 5 | 62 |
| 22379 | 1 | 66 | 0.02 | 25564 | 2 | 30 | 0.07 | 29181 | 4 | 32 |
| 22394 | 5 | 28 | 0.18 | 25567 | 5 | 30 | 0.17 | 29189 | 5 | 25 |
| 22395 | 20 | 63 | 0.32 | 25571 | 6 | 72 | 0.08 | 29228 | 10 | 25 |
| 22405 | 20 | 30 | 0.67 | 25620 | 5 | 21 | 0.24 | 29254 | 10 | 34 |
| 22407 | 4 | 92 | 0.04 | 25629 | 15 | 52 | 0.29 | 29262 | 5 | 30 |
| 22409 | 4 | 62 | 0.06 | 25633 | 6 | 32 | 0.19 | 29268 | 5 | 33 |
| 22412 | 2 | 30 | 0.07 | 25634 | 20 | 33 | 0.61 | 29271 | 3 | 64 |
| 22420 | 8 | 34 | 0.24 | 25642 | 20 | 40 | 0.50 | 29274 | 8 | 48 |
| 22423 | 15 | 36 | 0.42 | 25645 | 1 | 22 | 0.05 | 29301 | 10 | 55 |
| 22432 | 2 | 94 | 0.02 | 25653 | 12 | 31 | 0.39 | 29313 | 6 | 41 |
| 22449 | 20 | 28 | 0.71 | 25663 | 7 | 8 | 0.88 | 29320 | 1 | 33 |
| 22452 | 5 | 42 | 0.12 | 25665 | 15 | 42 | 0.36 | 29322 | 10 | 35 |
| 22468 | 1 | 65 | 0.02 | 25667 | 3 | 41 | 0.07 | 29350 | 12 | 35 |
| 22482 | 17 | 57 | 0.30 | 25671 | 5 | 14 | 0.36 | 29373 | 2 | 18 |
| 22492 | 10 | 5 | 2.00 | 25684 | 20 | 51 | 0.39 | 29383 | 3 | 60 |
| 22498 | 10 | 61 | 0.16 | 25689 | 4 | 42 | 0.10 | 29384 | 5 | 9 |
| 22526 | 2 | 56 | 0.04 | 25692 | 2 | 22 | 0.09 | 29386 | 10 | 35 |
| 22529 | 2 | 87 | 0.02 | 25697 | 10 | 25 | 0.40 | 29393 | 5 | 3 |
| 22530 | 3 | 30 | 0.10 | 25702 | 15 | 57 | 0.26 | 29398 | 2 | 25 |
| 22534 | 1 | 33 | 0.03 | 25707 | 3 | 29 | 0.10 | 29431 | 2 | 33 |
| 22536 | 10 | 83 | 0.12 | 25719 | 3 | 29 | 0.10 | 29457 | 3 | 35 |
| 22548 | 10 | 78 | 0.13 | 25739 | 10 | 32 | 0.31 | 29458 | 6 | 42 |
| 22549 | 3 | 30 | 0.10 | 25748 | 20 | 25 | 0.80 | 29459 | 15 | 33 |
| 22553 | 10 | 60 | 0.17 | 25751 | 10 | 53 | 0.19 | 29468 | 12 | 41 |
| 22562 | 2 | 30 | 0.07 | 25754 | 7 | 28 | 0.25 | 29477 | 2 | 59 |
| 22568 | 3 | 8 | 0.38 | 25756 | 5 | 30 | 0.17 | 29495 | 21 | 34 |
| 22569 | 2 | 50 | 0.04 | 25760 | 10 | 45 | 0.22 | 29498 | 2 | 26 |

Fig.4 (continued)

| 22582 | 32 | 33 | 0.97 | 25762 | 10 | 36 | 0.28 | 29503 | 5 | 45 |
|---|---|---|---|---|---|---|---|---|---|---|
| 22587 | 1 | 30 | 0.03 | 25765 | 8 | 29 | 0.28 | 29513 | 20 | 53 |
| 22601 | 3 | 102 | 0.03 | 25767 | 1 | 53 | 0.02 | 29548 | 7 | 25 |
| 22605 | 18 | 84 | 0.21 | 25772 | 2 | 9 | 0.22 | 29559 | 10 | 47 |
| 22609 | 5 | 30 | 0.17 | 25774 | 17 | 77 | 0.22 | 29560 | 1 | 34 |
| 22623 | 2 | 21 | 0.10 | 25796 | 5 | 14 | 0.36 | 29562 | 5 | 38 |
| 22635 | 6 | 28 | 0.21 | 25798 | 4 | 32 | 0.13 | 29566 | 7 | 34 |
| 22638 | 6 | 60 | 0.10 | 25827 | 0.5 | 19 | 0.03 | 29576 | 1 | 26 |
| 22639 | 2 | 76 | 0.03 | 25829 | 5 | 41 | 0.12 | 29581 | 12 | 26 |
| 22645 | 22 | 47 | 0.47 | 25836 | 5 | 33 | 0.15 | 29586 | 5 | 35 |
| 22647 | 1 | 34 | 0.03 | 25854 | 5 | 54 | 0.09 | 29593 | 9 | 48 |
| 22648 | 1 | 21 | 0.05 | 25869 | 4 | 31 | 0.13 | 29604 | 3 | 20 |
| 22653 | 5 | 40 | 0.13 | 25872 | 50 | 32 | 1.56 | 29615 | 8 | 20 |
| 22657 | 10 | 22 | 0.45 | 25873 | 3 | 38 | 0.08 | 29630 | 4 | 11 |
| 22659 | 15 | 63 | 0.24 | 25886 | 3 | 21 | 0.14 | 29636 | 3 | 35 |
| 22664 | 7 | 63 | 0.11 | 25889 | 2 | 10 | 0.20 | 29637 | 14 | 24 |
| 22668 | 3 | 26 | 0.12 | 25891 | 3 | 61 | 0.05 | 29640 | 5 | 42 |
| 22675 | 1 | 48 | 0.02 | 25894 | 10 | 2 | 5.00 | 29647 | 10 | 63 |
| 22686 | 28 | 89 | 0.31 | 25896 | 12 | 50 | 0.24 | 29653 | 17 | 43 |
| 22687 | 20 | 83 | 0.24 | 25899 | 4 | 30 | 0.13 | 29664 | 25 | 30 |
| 22689 | 6 | 28 | 0.21 | 25923 | 15 | 58 | 0.26 | 29665 | 5 | 33 |
| 22705 | 3 | 64 | 0.05 | 25924 | 8 | 62 | 0.13 | 29669 | 20 | 35 |
| 22719 | 4 | 8 | 0.50 | 25928 | 5 | 24 | 0.21 | 29677 | 5 | 33 |
| 22725 | 4 | 34 | 0.12 | 25948 | 8 | 60 | 0.13 | 29678 | 5 | 39 |
| 22739 | 16 | 37 | 0.43 | 25950 | 5 | 36 | 0.14 | 29687 | 11 | 52 |
| 22756 | 5 | 62 | 0.08 | 25952 | 5 | 38 | 0.13 | 29693 | 25 | 31 |
| 22757 | 5 | 52 | 0.10 | 25956 | 1 | 30 | 0.03 | 29698 | 1 | 2 |
| 22761 | 10 | 30 | 0.33 | 25964 | 10 | 38 | 0.26 | 29699 | 3 | 32 |
| 22763 | 10 | 34 | 0.29 | 25977 | 10 | 18 | 0.56 | 29705 | 12 | 50 |
| 22771 | 10 | 56 | 0.18 | 25995 | 12 | 45 | 0.27 | 29725 | 8 | 32 |
| 22775 | 20 | 54 | 0.37 | 26009 | 15 | 62 | 0.24 | 29736 | 6 | 30 |
| 22777 | 23 | 54 | 0.43 | 26010 | 15 | 60 | 0.25 | 29738 | 2 | 48 |
| 22783 | 2 | 19 | 0.11 | 26012 | 2 | 34 | 0.06 | 29772 | 2 | 9 |
| 22786 | 3 | 33 | 0.09 | 26025 | 20 | 38 | 0.53 | 29785 | 13 | 58 |
| 22788 | 21 | 69 | 0.30 | 26032 | 5 | 42 | 0.12 | 29811 | 10 | 7 |
| 22795 | 3 | 90 | 0.03 | 26033 | 7 | 17 | 0.41 | 29842 | 15 | 49 |
| 22800 | 3 | 38 | 0.08 | 26042 | 5 | 28 | 0.18 | 29875 | 45 | 33 |
| 22806 | 16 | 55 | 0.29 | 26044 | 3 | 32 | 0.09 | 29881 | 2 | 23 |
| 22807 | 12 | 24 | 0.50 | 26051 | 3 | 42 | 0.07 | 29917 | 5 | 53 |

Fig.4 (continued)

| 22813 | 10 | 28 | 0.36 | 26055 | 20 | 4 | 5.00 | 29923 | 1 | 34 |
|---|---|---|---|---|---|---|---|---|---|---|
| 22835 | 4 | 29 | 0.14 | 26059 | 5 | 29 | 0.17 | 29926 | 7 | 36 |
| 22843 | 5 | 34 | 0.15 | 26064 | 15 | 38 | 0.39 | 29927 | 10 | 35 |
| 22848 | 15 | 33 | 0.45 | 26069 | 10 | 40 | 0.25 | 29940 | 2 | 38 |
| 22852 | 15 | 33 | 0.45 | 26076 | 10 | 78 | 0.13 | 29948 | 2 | 50 |
| 22864 | 5 | 22 | 0.23 | 26087 | 3 | 38 | 0.08 | 29950 | 5 | 31 |
| 22866 | 20 | 42 | 0.48 | 26090 | 10 | 44 | 0.23 | 29951 | 10 | 32 |
| 22867 | 8 | 55 | 0.15 | 26097 | 4 | 49 | 0.08 | 29973 | 10 | 43 |
| 22908 | 18 | 38 | 0.47 | 26100 | 9 | 26 | 0.35 | 29982 | 5 | 37 |
| 22911 | 2 | 89 | 0.02 | 26102 | 10 | 15 | 0.67 | 29985 | 2 | 43 |
| 22921 | 5 | 24 | 0.21 | 26117 | 8 | 76 | 0.11 | 29995 | 16 | 27 |
| 22928 | 5 | 31 | 0.16 | 26119 | 5 | 55 | 0.09 | 30001 | 4 | 32 |
| 22949 | 6 | 35 | 0.17 | 26142 | 5 | 19 | 0.26 | 30009 | 3 | 62 |
| 22951 | 2 | 2 | 1.00 | 26145 | 15 | 39 | 0.38 | 30010 | 10 | 43 |
| 22953 | 4 | 94 | 0.04 | 26168 | 1 | 55 | 0.02 | 30029 | 20 | 47 |
| 22960 | 18 | 62 | 0.29 | 26178 | 135 | 69 | 1.96 | 30038 | 15 | 22 |
| 22970 | 3 | 51 | 0.06 | 26187 | 1 | 4 | 0.25 | 30085 | 20 | 33 |
| 22979 | 2 | 18 | 0.11 | 26202 | 10 | 37 | 0.27 | 30102 | 2 | 30 |
| 22980 | 8 | 29 | 0.28 | 26206 | 10 | 62 | 0.16 | 30112 | 6 | 30 |
| 22985 | 5 | 26 | 0.19 | 26211 | 10 | 32 | 0.31 | 30120 | 10 | 19 |
| 22990 | 5 | 58 | 0.09 | 26219 | 2 | 38 | 0.05 | 30125 | 1 | 26 |
| 23001 | 10 | 84 | 0.12 | 26245 | 2 | 38 | 0.05 | 30127 | 10 | 32 |
| 23003 | 20 | 39 | 0.51 | 26254 | 6 | 62 | 0.10 | 30134 | 8 | 32 |
| 23004 | 15 | 37 | 0.41 | 26259 | 25 | 55 | 0.45 | 30148 | 10 | 43 |
| 23016 | 10 | 2 | 5.00 | 26277 | 15 | 38 | 0.39 | 30157 | 15 | 21 |
| 23022 | 15 | 62 | 0.24 | 26282 | 5 | 25 | 0.20 | 30159 | 3 | 29 |
| 23030 | 8 | 39 | 0.21 | 26294 | 18 | 55 | 0.33 | 30161 | 1 | 51 |
| 23033 | 5 | 30 | 0.17 | 26297 | 3 | 44 | 0.07 | 30163 | 8 | 28 |
| 23035 | 10 | 20 | 0.50 | 26305 | 5 | 33 | 0.15 | 30165 | 3 | 22 |
| 23039 | 5 | 32 | 0.16 | 26330 | 5 | 48 | 0.10 | 30166 | 5 | 35 |
| 23044 | 10 | 62 | 0.16 | 26331 | 4 | 15 | 0.27 | 30176 | 2 | 3 |
| 23045 | 8 | 30 | 0.27 | 26342 | 10 | 37 | 0.27 | 30201 | 2 | 28 |
| 23062 | 5 | 85 | 0.06 | 26343 | 5 | 28 | 0.18 | 30223 | 10 | 29 |
| 23070 | 4 | 32 | 0.13 | 26355 | 2 | 60 | 0.03 | 30225 | 5 | 38 |
| 23078 | 7 | 70 | 0.10 | 26356 | 6 | 36 | 0.17 | 30244 | 2 | 22 |
| 23090 | 13 | 17 | 0.76 | 26364 | 2 | 23 | 0.09 | 30271 | 12 | 32 |
| 23100 | 5 | 37 | 0.14 | 26374 | 10 | 54 | 0.19 | 30298 | 3 | 33 |
| 23103 | 5 | 24 | 0.21 | 26377 | 5 | 50 | 0.10 | 30307 | 1 | 1 |
| 23109 | 6 | 17 | 0.35 | 26379 | 1 | 25 | 0.04 | 30316 | 1 | 4 |

Fig.4 (continued)

| 23118 | 1 | 34 | 0.03 | 26381 | 5 | 39 | 0.13 | 30341 | 20 | 58 |
|---|---|---|---|---|---|---|---|---|---|---|
| 23119 | 10 | 33 | 0.30 | 26386 | 10 | 37 | 0.27 | 30360 | 3 | 31 |
| 23123 | 15 | 85 | 0.18 | 26389 | 5 | 60 | 0.08 | 30383 | 5 | 56 |
| 23127 | 10 | 30 | 0.33 | 26393 | 8 | 31 | 0.26 | 30388 | 10 | 33 |
| 23133 | 5 | 14 | 0.36 | 26401 | 2 | 28 | 0.07 | 30408 | 2 | 32 |
| 23134 | 10 | 32 | 0.31 | 26405 | 3 | 37 | 0.08 | 30420 | 7 | 49 |
| 23137 | 3 | 49 | 0.06 | 26411 | 5 | 39 | 0.13 | 30467 | 10 | 2 |
| 23141 | 15 | 57 | 0.26 | 26429 | 2 | 47 | 0.04 | 30488 | 6 | 34 |
| 23145 | 17 | 92 | 0.18 | 26437 | 10 | 67 | 0.15 | 30520 | 5 | 61 |
| 23158 | 2 | 33 | 0.06 | 26455 | 15 | 52 | 0.29 | 30524 | 10 | 35 |
| 23165 | 5 | 58 | 0.09 | 26461 | 22 | 59 | 0.37 | 30533 | 17 | 34 |
| 23170 | 3 | 32 | 0.09 | 26469 | 15 | 3 | 5.00 | 30536 | 3 | 31 |
| 23184 | 8 | 21 | 0.38 | 26475 | 12 | 44 | 0.27 | 30567 | 6 | 33 |
| 23185 | 8 | 40 | 0.20 | 26494 | 10 | 64 | 0.16 | 30578 | 2 | 36 |
| 23193 | 12.5 | 54 | 0.23 | 26498 | 2 | 25 | 0.08 | 30583 | 5 | 34 |
| 23195 | 1 | 24 | 0.04 | 26503 | 5 | 46 | 0.11 | 30586 | 20 | 33 |
| 23206 | 10 | 47 | 0.21 | 26504 | 5 | 56 | 0.09 | 30635 | 10 | 48 |
| 23211 | 3 | 60 | 0.05 | 26511 | 2 | 65 | 0.03 | 30648 | 5 | 30 |
| 23224 | 10 | 24 | 0.42 | 26522 | 12 | 60 | 0.20 | 30650 | 15 | 60 |
| 23229 | 22 | 60 | 0.37 | 26523 | 15 | 43 | 0.35 | 30657 | 3 | 23 |
| 23244 | 2 | 22 | 0.09 | 26530 | 15 | 36 | 0.42 | 30666 | 2 | 17 |
| 23245 | 2 | 23 | 0.09 | 26539 | 15 | 63 | 0.24 | 30693 | 10 | 33 |
| 23251 | 10 | 16 | 0.63 | 26546 | 3 | 28 | 0.11 | 30699 | 10 | 24 |
| 23259 | 20 | 15 | 1.33 | 26553 | 24 | 47 | 0.51 | 30714 | 10 | 15 |
| 23263 | 1 | 18 | 0.06 | 26562 | 15 | 44 | 0.34 | 30718 | 15 | 28 |
| 23269 | 15 | 32 | 0.47 | 26570 | 3 | 40 | 0.08 | 30727 | 6 | 25 |
| 23277 | 2 | 91 | 0.02 | 26596 | 15 | 30 | 0.50 | 30729 | 25 | 33 |
| 23283 | 9 | 93 | 0.10 | 26597 | 20 | 65 | 0.31 | 30730 | 15 | 58 |
| 23288 | 30 | 60 | 0.50 | 26609 | 7 | 53 | 0.13 | 30735 | 8 | 33 |
| 23289 | 5 | 4 | 1.25 | 26628 | 7 | 69 | 0.10 | 30736 | 2 | 20 |
| 23293 | 6 | 33 | 0.18 | 26633 | 3 | 30 | 0.10 | 30757 | 3 | 14 |
| 23305 | 4 | 34 | 0.12 | 26635 | 13 | 39 | 0.33 | 30758 | 15 | 52 |
| 23308 | 20 | 39 | 0.51 | 26643 | 10 | 24 | 0.42 | 30759 | 3 | 33 |
| 23310 | 7 | 31 | 0.23 | 26651 | 10 | 20 | 0.50 | 30772 | 2 | 26 |
| 23313 | 20 | 57 | 0.35 | 26652 | 5 | 12 | 0.42 | 30820 | 8 | 14 |
| 23338 | 9 | 66 | 0.14 | 26653 | 5 | 29 | 0.17 | 30821 | 2 | 15 |
| 23343 | 15 | 30 | 0.50 | 26656 | 5 | 30 | 0.17 | 30845 | 10 | 33 |
| 23348 | 6 | 32 | 0.19 | 26659 | 15 | 49 | 0.31 | 30858 | 4 | 33 |
| 23363 | 15 | 95 | 0.16 | 26682 | 3 | 41 | 0.07 | 30878 | 2 | 37 |

Fig.4 (continued)

| | | | | | | | | | |
|---|---|---|---|---|---|---|---|---|---|
| 23367 | 15 | 37 | 0.41 | 26685 | 15 | 55 | 0.27 | 30898 | 2 | 44 |
| 23385 | 1 | 28 | 0.04 | 26693 | 2 | 62 | 0.03 | 30907 | 6 | 33 |
| 23411 | 3 | 61 | 0.05 | 26701 | 5 | 13 | 0.38 | 30915 | 7 | 42 |
| 23417 | 3 | 22 | 0.14 | 26703 | 7 | 56 | 0.13 | 30924 | 8 | 32 |
| 23427 | 8 | 45 | 0.18 | 26713 | 20 | 62 | 0.32 | 30937 | 7 | 28 |
| 23431 | 7 | 63 | 0.11 | 26741 | 25 | 39 | 0.64 | 30944 | 10 | 33 |
| 23432 | 10 | 86 | 0.12 | 26747 | 6 | 74 | 0.08 | 30947 | 8 | 51 |
| 23433 | 5 | 76 | 0.07 | 26750 | 5 | 50 | 0.10 | 30952 | 7 | 5 |
| 23435 | 10 | 33 | 0.30 | 26754 | 30 | 58 | 0.52 | 30968 | 4 | 32 |
| 23439 | 3 | 93 | 0.03 | 26776 | 5 | 41 | 0.12 | 30974 | 3 | 33 |
| 23446 | 3 | 34 | 0.09 | 26777 | 8 | 22 | 0.36 | 30982 | 2 | 31 |
| 23466 | 14 | 35 | 0.40 | 26778 | 4 | 34 | 0.12 | 30987 | 15 | 24 |
| 23469 | 10 | 29 | 0.34 | 26819 | 10 | 34 | 0.29 | 30989 | 4 | 25 |
| 23483 | 10 | 8 | 1.25 | 26837 | 12 | 45 | 0.27 | 30991 | 6 | 24 |
| 23497 | 11.5 | 71 | 0.16 | 26841 | 25 | 51 | 0.49 | 31015 | 5 | 57 |
| 23501 | 3 | 22 | 0.14 | 26847 | 6 | 42 | 0.14 | 31028 | 8 | 14 |
| 23506 | 10 | 6 | 1.67 | 26854 | 16 | 40 | 0.40 | 31043 | 4 | 24 |
| 23516 | 10 | 22 | 0.45 | 26869 | 5 | 21 | 0.24 | 31049 | 2 | 20 |
| 23518 | 5 | 58 | 0.09 | 26879 | 5 | 8 | 0.63 | 31065 | 5 | 33 |
| 23524 | 7 | 64 | 0.11 | 26894 | 1 | 21 | 0.05 | 31080 | 2 | 32 |
| 23540 | 3 | 24 | 0.13 | 26905 | 2 | 47 | 0.04 | 31096 | 5 | 31 |
| 23556 | 5 | 27 | 0.19 | 26906 | 3 | 29 | 0.10 | 31128 | 5 | 13 |
| 23560 | 7 | 47 | 0.15 | 26911 | 2 | 30 | 0.07 | 31133 | 3 | 17 |
| 23565 | 7 | 32 | 0.22 | 26934 | 10 | 57 | 0.18 | 31134 | 15 | 57 |
| 23584 | 2 | 50 | 0.04 | 26936 | 14 | 58 | 0.24 | 31142 | 1 | 41 |
| 23585 | 1 | 33 | 0.03 | 26941 | 15 | 33 | 0.45 | 31153 | 3 | 7 |
| 23600 | 7 | 22 | 0.32 | 26946 | 3 | 29 | 0.10 | 31154 | 5 | 40 |
| 23613 | 6 | 28 | 0.21 | 26952 | 8 | 43 | 0.19 | 31155 | 4 | 55 |
| 23621 | 7 | 71 | 0.10 | 26954 | 3 | 58 | 0.05 | 31156 | 5 | 33 |
| 23623 | 15 | 53 | 0.28 | 26961 | 2 | 28 | 0.07 | 31182 | 5 | 29 |
| 23625 | 1 | 29 | 0.03 | 26965 | 5 | 44 | 0.11 | 31200 | 20 | 50 |
| 23627 | 20 | 33 | 0.61 | 26979 | 5 | 28 | 0.18 | 31245 | 10 | 49 |
| 23635 | 1 | 35 | 0.03 | 27012 | 1 | 3 | 0.33 | 31251 | 12 | 28 |
| 23655 | 4 | 19 | 0.21 | 27024 | 13 | 32 | 0.41 | 31252 | 10 | 35 |
| 23661 | 5 | 28 | 0.18 | 27040 | 2 | 69 | 0.03 | 31259 | 10 | 15 |
| 23675 | 40 | 41 | 0.98 | 27046 | 15 | 63 | 0.24 | 31270 | 1 | 8 |
| 23685 | 4 | 26 | 0.15 | 27048 | 2 | 32 | 0.06 | 31275 | 16 | 51 |
| 23687 | 9 | 54 | 0.17 | 27056 | 16 | 48 | 0.33 | 31277 | 4 | 6 |
| 23697 | 10 | 94 | 0.11 | 27060 | 7 | 12 | 0.58 | 31280 | 10 | 35 |

Fig.4 (continued)

| 23706 | 5  | 20 | 0.25 | 27062 | 10 | 12 | 0.83 | 31285 | 22 | 39 |
|-------|----|----|------|-------|----|----|------|-------|----|----|
| 23716 | 20 | 17 | 1.18 | 27064 | 10 | 44 | 0.23 | 31295 | 7  | 23 |
| 23717 | 2  | 30 | 0.07 | 27068 | 10 | 30 | 0.33 | 31304 | 10 | 34 |
| 23719 | 10 | 63 | 0.16 | 27070 | 9  | 34 | 0.26 | 31326 | 4  | 52 |
| 23729 | 1  | 25 | 0.04 | 27072 | 3  | 32 | 0.09 | 31334 | 7  | 33 |
| 23737 | 1  | 47 | 0.02 | 27074 | 2  | 35 | 0.06 | 31335 | 5  | 33 |
| 23745 | 10 | 89 | 0.11 | 27079 | 2  | 28 | 0.07 | 31339 | 10 | 45 |
| 23769 | 10 | 32 | 0.31 | 27103 | 20 | 65 | 0.31 | 31369 | 20 | 55 |
| 23783 | 5  | 47 | 0.11 | 27137 | 12 | 70 | 0.17 | 31383 | 9  | 34 |
| 23785 | 11 | 33 | 0.33 | 27138 | 7  | 34 | 0.21 | 31406 | 1  | 5  |
| 23788 | 1  | 35 | 0.03 | 27144 | 15 | 56 | 0.27 | 31425 | 10 | 35 |
| 23790 | 20 | 58 | 0.34 | 27165 | 3  | 68 | 0.04 | 31432 | 3  | 47 |
| 23792 | 2  | 4  | 0.50 | 27174 | 2  | 14 | 0.14 | 31439 | 7  | 35 |
| 23793 | 10 | 69 | 0.14 | 27184 | 15 | 28 | 0.54 | 31462 | 1  | 18 |
| 23797 | 6  | 33 | 0.18 | 27198 | 6  | 42 | 0.14 | 31472 | 5  | 35 |
| 23799 | 10 | 19 | 0.53 | 27203 | 1  | 26 | 0.04 | 31483 | 5  | 35 |
| 23802 | 35 | 90 | 0.39 | 27207 | 20 | 42 | 0.48 | 31486 | 5  | 41 |
| 23806 | 4  | 89 | 0.04 | 27217 | 3  | 65 | 0.05 | 31493 | 35 | 55 |
| 23807 | 6  | 41 | 0.15 | 27234 | 7  | 43 | 0.16 | 31495 | 5  | 35 |
| 23811 | 3  | 62 | 0.05 | 27239 | 5  | 33 | 0.15 | 31498 | 7  | 20 |
| 23840 | 9  | 92 | 0.10 | 27273 | 3  | 58 | 0.05 | 31503 | 22 | 56 |
| 23843 | 5  | 34 | 0.15 | 27285 | 11 | 35 | 0.31 | 31508 | 15 | 34 |
| 23846 | 10 | 41 | 0.24 | 27290 | 20 | 7  | 2.86 | 31514 | 15 | 46 |
| 23848 | 3  | 47 | 0.06 | 27297 | 3  | 34 | 0.09 | 31517 | 20 | 47 |
| 23852 | 20 | 21 | 0.95 | 27305 | 6  | 55 | 0.11 | 31526 | 2  | 15 |
| 23861 | 6  | 30 | 0.20 | 27309 | 1  | 18 | 0.06 | 31527 | 8  | 36 |
| 23865 | 3  | 34 | 0.09 | 27310 | 1  | 33 | 0.03 | 31532 | 5  | 37 |
| 23872 | 2  | 22 | 0.09 | 27336 | 15 | 20 | 0.75 | 31547 | 4  | 31 |
| 23876 | 4  | 35 | 0.11 | 27344 | 10 | 33 | 0.30 | 31557 | 5  | 33 |
| 23878 | 20 | 80 | 0.25 | 27347 | 3  | 39 | 0.08 | 31589 | 6  | 40 |
| 23882 | 8  | 18 | 0.44 | 27357 | 15 | 33 | 0.45 | 31600 | 2  | 51 |
| 23892 | 45 | 33 | 1.36 | 27368 | 9  | 33 | 0.27 | 31605 | 8  | 52 |
| 23900 | 15 | 30 | 0.50 | 27376 | 20 | 19 | 1.05 | 31618 | 6  | 31 |
| 23928 | 12 | 43 | 0.28 | 27380 | 10 | 56 | 0.18 | 31636 | 3  | 28 |
| 23931 | 11 | 36 | 0.31 | 27387 | 2  | 13 | 0.15 | 31693 | 15 | 44 |
| 23934 | 2  | 14 | 0.14 | 27390 | 20 | 36 | 0.56 | 31714 | 12 | 33 |
| 23935 | 7  | 35 | 0.20 | 27400 | 2  | 26 | 0.08 | 31717 | 3  | 18 |
| 23941 | 3  | 80 | 0.04 | 27412 | 50 | 66 | 0.76 | 31740 | 2  | 15 |
| 23947 | 25 | 75 | 0.33 | 27427 | 15 | 16 | 0.94 | 31748 | 8  | 24 |

Fig.4 (continued)

| | | | | | | | | | |
|---|---|---|---|---|---|---|---|---|---|
| 23959 | 7 | 30 | 0.23 | 27447 | 20 | 27 | 0.74 | 31767 | 5 | 34 |
| 23963 | 4 | 20 | 0.20 | 27454 | 2 | 59 | 0.03 | 31777 | 4 | 16 |
| 23964 | 4 | 5 | 0.80 | 27463 | 15 | 60 | 0.25 | 31798 | 12 | 32 |
| 23969 | 2 | 31 | 0.06 | 27465 | 2 | 56 | 0.04 | 31816 | 15 | 47 |
| 23980 | 10 | 43 | 0.23 | 27473 | 10 | 35 | 0.29 | 31819 | 15 | 34 |
| 23981 | 15 | 45 | 0.33 | 27494 | 30 | 63 | 0.48 | 31840 | 5 | 37 |
| 23992 | 8 | 72 | 0.11 | 27502 | 3 | 68 | 0.04 | 31846 | 10 | 54 |
| 23994 | 5 | 20 | 0.25 | 27521 | 3 | 27 | 0.11 | 31848 | 5 | 21 |
| 23998 | 10 | 26 | 0.38 | 27525 | 25 | 59 | 0.42 | 31855 | 10 | 36 |
| 24000 | 12 | 62 | 0.19 | 27528 | 4 | 59 | 0.07 | 31870 | 6 | 30 |
| 24025 | 5 | 73 | 0.07 | 27538 | 19 | 56 | 0.34 | 31882 | 2 | 32 |
| 24028 | 9 | 62 | 0.15 | 27541 | 22 | 33 | 0.67 | 31887 | 10 | 33 |
| 24042 | 10 | 32 | 0.31 | 27601 | 6 | 27 | 0.22 | 31900 | 6 | 15 |
| 24053 | 5 | 48 | 0.10 | 27611 | 8 | 34 | 0.24 | 31940 | 10 | 45 |
| 24055 | 8 | 52 | 0.15 | 27612 | 5 | 33 | 0.15 | 31984 | 2 | 35 |
| 24065 | 7 | 65 | 0.11 | 27616 | 3 | 29 | 0.10 | 32015 | 15 | 36 |
| 24080 | 5 | 36 | 0.14 | 27638 | 5 | 19 | 0.26 | 32027 | 5 | 9 |
| 24095 | 1 | 44 | 0.02 | 27648 | 20 | 12 | 1.67 | 32032 | 15 | 24 |
| 24097 | 10 | 33 | 0.30 | 27658 | 3 | 33 | 0.09 | 32033 | 2 | 15 |

Fig. 6

Average Rate of Gain (lbs/day)

| | |
|---|---|
| Echinacea Extracts Only | 0.242 |
| Echinacea Extracts with Zinc, Vitamin D3 and Ternary Blend | 0.306 |
| Change | 26.4% |

Standard Error

| | |
|---|---|
| Echinacea Extracts Only | 0.0101 |
| Echinacea Extracts with Zinc, Vitamin D3 and Ternary Blend | 0.0116 |

Significance

| | |
|---|---|
| P-value (<.0001) | 0.000066 |

METHOD AND NUTRITIONAL SUPPLEMENT FOR ENHANCING WEIGHT GAIN OF A MAMMAL

FIELD OF THE DISCLOSURE

The present invention generally relates to a nutritional supplement and method for enhancing weight gain of a mammal, particularly to a nutritional supplement made from *Echinacea* extracts which increases the appetite and slows the metabolism of the mammal by activating cannabinoid receptor type 1 of the mammal.

BACKGROUND

While the obesity epidemic is spreading at an alarming rate in the modern world especially in the developed countries, there are also a segment of individuals suffering from underweight which get far less attention. Not only will serious underweight create undesirable appearance, it may also result from eating disorders, digestive disorders and depression.

The American Dietetic Association (ADA) defines the ideal body mass index (BMI) as between 20 and 25. Anyone below that range would be considered underweight and those with a BMI from 18.5 and below extremely underweight. The ability for a person to gain or lose weight depends primarily on the person's intake of calories. Calories are found in food. However, the calories in food come in different forms: carbohydrates, fats, and protein. These different forms, known as "macronutrients," have different effects on the body and its ability to gain weight.

When the person eats more calories than his or her body burns, the extra calories get stored for future use in the form of muscle or fat tissue. Conversely, when the person eats fewer calories than his or her body burns, the person's body taps into stored muscle and fat tissue to get the energy it needs. As a result, a major cause for certain individuals to find gaining weight difficult is a weak appetite or fast metabolism, in addition to eating irregularly due to work, or eating healthy food having low caloric density.

Conventionally, people who tried to gain weight took commercial weight gain shakes as a convenient source of calories. However, high calorie shakes are very filling and may prevent these people from enjoying regular meals by blunting their appetite, causing them to eat little or no food later in the day and resulting in little or no change in body weight.

There are also literatures suggesting that taking multivitamin supplements can improve a person's weight gain. However, such a method is only effective when the person's capability of gaining weight was being affected by certain nutrient deficiencies. People who are not deficient in given nutrients will often find this method ineffective in gaining weight. In fact, most recent research suggests that multivitamin supplementation has no effect on body weight in the general population or that it may actually prevent weight gain. See, e.g., Major, G. C., "Multivitamin and dietary supplements, body weight and appetite: results from a cross-sectional and a randomized double-blind placebo-controlled study" The British journal of nutrition, 5, 1157-1167 (2007); Nachtigal, M. C., "Dietary supplements and weight control in a middle-age population. Journal of alternative and complementary medicine" (New York, N.Y.), 5, 909-915 (2005).

Despite the foregoing efforts to improve weight gain for individuals, conventional methods are not ideally suited for everyone. Accordingly, there exists a need for improved method and formulation for enhancing weight gain which obviates the deficiency of conventional methods.

BRIEF DESCRIPTION OF THE DRAWINGS

FIG. 1 provides the formulation of specific *Echinacea* formulations that are in accordance with at least one embodiment of the present disclosure.

FIG. 2 provides the formulation of specific *Echinacea* formulations that are in accordance with at least one embodiment of the present disclosure.

FIG. 3 is a table of data collected from approximately 1200 test subjects showing their weight gain and other related information after taking a formulation containing only *Echinacea* extracts.

FIG. 4 is a table of data collected from approximately 1200 other test subjects showing their weight gain and other related information after taking formulation with *Echinacea* extracts, Vitamin D3, Zinc, Lecithin, Vitamin C and Vitamin E.

FIG. 6 is a table which lists the amount of average rate of gain (lbs/day) for the two formulations.

SUMMARY OF THE INVENTION

Figure 5:
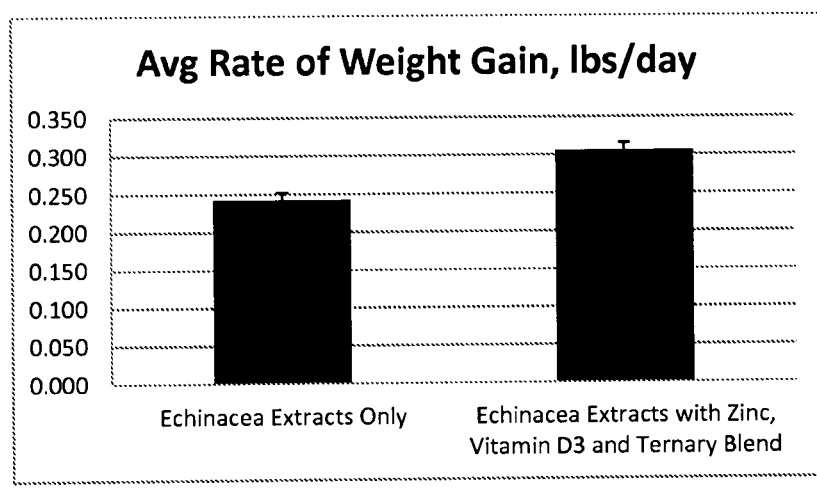
FIG. 5 is a bar chart which compares the average rate of weight gain (lbs/day) between subjects that took *Echinacea* extracts only and subjects that took *Echinacea* extracts with Vitamin D3, Zinc and Ternary Blend. The data reveals that the latter provides approximately 26.4% more weight gain as compared to the only *Echinacea* extracts formulation.

The present invention overcomes the shortcomings of conventional methods of gaining weight by providing a method and nutritional supplement which stimulates appetite and slows metabolism, thereby enhancing weight gain for a mammal. The method and nutritional supplement disclosed by the present invention also effectively increases the bodyweight of the mammal even if the mammal already has a normal bodyweight.

In accordance with one aspect of at least one embodiment of the present invention, the method of enhancing weight gain of a mammal comprises administering to the mammal an effective amount of at least two types of alkamide or isobutylamide compounds extracted or otherwise derived from *Echinacea* species along with an antioxidant and optionally minerals. Specifically, the alkamide or isobutylamide compounds used are selected from group consisting of Dodeca-2E,4E,8Z,10E/Z-tetraenoic acid isobutylamides; Dodeca-2E,4Z-diene-8,10-diynoic acid isobutylamide; Undeca-2Z,4E-diene-8,10-diynoic acid isobutylamide; Undeca-2-ene-8,10-diynoic acid isobutylamide; Dodeca-2E,4E-dienoic acid isobutylamide; Dodeca-2E-ene-8,10-diynoic acid 2-methylbutylamide; Dodeca-2E,4E,8Z-trienoic acid isobutylamide; Pentadeca-2E,9Z-diene-12,14-diynoic acid isobutylamide; and Dodeca-2E,4Z-diene-8,10-diynoic acid isobutylamide.

In accordance with another aspect of at least one embodiment of the present invention, the nutritional supplement of the present invention comprises an antioxidant and at least two types of alkamide or isobutylamide compound extracted from *Echinacea* species selected from group consisting of *Echinacea angustifolia, Echinacea atrorubens, Echinacea laevigata, Echinacea pallida, Echinacea paradoxa, Echinacea purpurea, Echinacea sanguinea, Echinacea simulate* and *Echinacea tennesseensis*. Minerals such as zinc and magnesium can optionally be added to the nutritional supplement to provide even better effect.

These and other features, aspects and advantages of the present invention will become better understood with reference to the following drawings, description and claims.

DETAILED DESCRIPTION OF THE INVENTION

The following description is not to be taken in a limiting sense, but is made merely for the purpose of illustrating the general principles of the invention, since the scope of the invention is best defined by the following claims. Various inventive features are described below that can each be used independently of one another or in combination with other features.

For purposes of the present disclosure, terms "CB1" and "CB2" should mean cannabinoid receptor type-1 and type-2 respectively. The cannabinoid receptor type-1 and type-2, often abbreviated as CB1 and CB2 respectively, have been identified as biological receptors of mammals. CB1 receptors are expressed in neurons of the central and peripheral nervous system. CB2 receptors are found almost exclusively in peripheral immune cells. The CB1 receptor has been found to be active in several areas of the body known to stimulate eating behavior. CB1 activation has powerful effects on food intake, energy balance, and metabolism. Activity at the receptor is critical for regulation of energy homeostasis and food intake. CB1 receptors in the brain and periphery have already been targeted as a treatment for obesity. The pharmaceutical drug rimonabant, which was FDA approved in 1996, was found to effectively reduce food intake and decrease body weight by blocking activity at the CB1 receptor as a competitive antagonist. In contrast, activation of the CB1 receptor by the endocannabinoids or by exogenous phytocannabinoids are well established to produce stimulatory effects on appetite, food intake, and weight gain. The term "*Echinacea* extract" or "*Echinacea* constituent" generally refers to alkamide or isobutylamide compound extracted or derived from *Echinacea* species.

Broadly, embodiments of the present invention generally provide method and nutritional supplement for enhancing weight gain of a mammal by activating CB1 of the mammal. Specifically, the present invention achieved its purpose by administering to the mammal an effective amount of alkamide compound, isobutylamide compound or combination thereof derived, extracted, or prepared from *Echinacea* species that are CB1 receptor agonist.

It was observed that *Echinacea* alkamides are structurally similar to the endocannabinoid AEA. Subsequent cannabinoid receptor binding studies have confirmed that all of the alkamides in *Echinacea* have affinity for the CB1 receptor at micromolar (µM) dissociation constants. The endocannabinoid system is a target for alkamides from *Echinacea* species. While the alkamides in *Echinacea* species have been shown to bind to CB1 receptors, and while CB1 activation has been implicated generally in appetite and metabolic regulation, no published studies or academic papers could be located in which alkamides were suggested or examined as a therapeutic target for the treatment of anorexia (insufficient appetite) or underweight.

The pharmacokinetic properties of the alkamides in *Echinacea* have been examined. Experiments show that the alkamides are detectable in human blood within 10 minutes of oral application. Time to peak concentration varied from 20-30 minutes. Orally ingested *Echinacea* preparations are capable of providing bioavailable alkamides for bioactivity at the CB1 receptor.

The alkamide or isobutylamide compounds extracted from *Echinacea* species that are found to be effective in activating CB1 include, but are not limited to, Dodeca-2E,4E,8Z,10E/Z-tetraenoic acid isobutylamides; Dodeca-2E,4Z-diene-8,10-diynoic acid isobutylamide; Undeca-2Z,4E-diene-8,10-diynoic acid isobutylamide; Undeca-2-ene-8,10-diynoic acid isobutylamide; Dodeca-2E,4E-dienoic acid isobutylamide; Dodeca-2E-ene-8,10-diynoic acid 2-methylbutylamide; Dodeca-2E,4E,8Z-trienoic acid isobutylamide; Pentadeca-2E,9Z-diene-12,14-diynoic acid isobutylamide; and Dodeca-2E,4Z-diene-8,10-diynoic acid isobutylamide.

These alkamide or isobutylamide compounds can be extracted or otherwise derived from the aerial parts, but ideally the roots, rhizomes or vegetative stems of *Echinacea* species (plants) such as *Echinacea angustifolia*, *Echinacea atrorubens*, *Echinacea laevigata*, *Echinacea pallida*, *Echinacea paradoxa*, *Echinacea purpurea*, *Echinacea sanguinea*, *Echinacea simulate* and *Echinacea tennesseensis*. For example, Dodeca-2E,4E,8Z,10E/Z-tetraenoic acid isobutylamides; Dodeca-2E,4Z-diene-8,10-diynoic acid isobutylamide; and Undeca-2Z,4E-diene-8,10-diynoic acid isobutylamide can be derived from *Echinacea purpurea* and Undeca-2-ene-8,10-diynoic acid isobutylamide and Dodeca-2E,4E-dienoic acid isobutylamide can be derived from *Echinacea augustifolia*.

The alkamide or isobutylamide compounds derived from *Echinacea* species are highly unsaturated compounds. Therefore, they are prone to oxidation. Many of the alkamides in *Echinacea* species contain one or two alkyne moieties, which are susceptible to degradation at higher temperature and oxygen levels. The medium-chained hydrocarbon portion of these alkamides contains one or more double bonds, and some alkamides have one or two acetylene bonds. None of the alkamides are saturated. As a result, alkamides should be prone to oxidation, especially in an environment rich in oxygen. It has been suggested that *Echinacea* roots should be left intact or the extracts be kept in solution to prevent the oxidative breakdown of the diene structures. One study found a 13% reduction in alkamide content of ground roots over 2 months. Another study of ground roots found that after 7 months, there was a reduction in alkamide content of 88% at 25° C. and 95% at 40° C. Another observed alkamide reduction in dried, crushed *Echinacea* stored in the light at 20° C. or in the dark at 30° C. over a period of 60 days.

The stability of the alkamide constituents of *Echinacea* is very important because the medicinal properties are determined by the biological viability of those constituents. One study proposed that another class of constituents in *Echinacea* known as the phenolics may act as antioxidants to decrease the degradation of alkamides in a dry extract. However, no published studies or academic papers could be located in which alkamides from *Echinacea* were preserved or proposed to be preserved by the addition of an antioxidant.

Thus, in one embodiment of the present invention, antioxidant is used with *Echinacea*-derived alkamides or isobutalamides to curtail the rate of oxidation and to decrease the rate of degradation, thus increasing shelf life and alkamide potency. The antioxidant that can be used includes, but is not limited to, alpha tocopherol (vitamin E), butylated hydroxyanisole (BHA), butylated hydroxytoluene (BHT), ascorbyl palmitate, propyl gallate, dodecyl gallate, ethyl gallate, and octyl gallate.

Alternatively, in another embodiment of the present invention, a unique ternary blend of antioxidant consisting of lecithin, vitamin C and vitamin E is disclosed for *Echinacea*-derived alkamides or isobutalamides. The ternary blend disclosed by the present invention effectively prevents *Echinacea*-derived alkamides or isobutylamides from oxidation and degradation, thereby enhancing their abilities to activate CB1 and shell-life. The vitamin C is preferably in the form of ascorbic acid rather than esters, salts or chelates. The vitamin E is preferably in the form of free tocopherols, and more ideally in the form of mixed tocopherols. In yet another embodiment of the present invention, it is preferred that the lecithin, vitamin C and vitamin E in the ternary blend have a ratio of 2:1:1 to 10:1:1 (lecithin:ascorbic acid:tocopherols); ideally, 4:1:1 to 5:1:1. When they are administered with *Echinacea*-derived isobutylamides or alkamides, it is preferred that their concentration is between 2,000 to 10,000 ppm, ideally 3,000 to 3,500 ppm. For example, an ideal concentration can be 2500 ppm:500 ppm:500 ppm (for lecithin, ascorbic acid and tocopherols) for a 3,500 ppm ternary blend.

In yet another embodiment of the present invention, the method of present invention further comprises administering the mammal with vitamin D. The vitamin D is preferably selected from group consisting of ergocalciferol (D2) and cholecalciferol (D3), and ideally includes cholecalciferol (D3). The preferred dosage is between 400 to 6000 IU (International Unit) per day, and ideally at least 4000 IU per day. The advantage of having vitamin D is that, in addition to well-known effects on calcium uptake, it may up-regulate intestinal glucose transport via SGLT1, thereby improving glucose and net macronutrient uptake. Vitamin D is also capable of inhibiting uncoupling protein 2 (UCP2), which facilitates mitochondrial proton leak and contributes to RMR. By inhibiting UCP2, vitamin D can reduce thermogenesis and metabolic rate, thereby promoting caloric surplus. Vitamin D is also known to be associated with β-cell function, systemic inflammation, insulin secretion, and insulin sensitivity. Thus, improved vitamin D status may improve glucose homeostasis and disposal, especially in mammals which are diabetic or pre-diabetic. In addition, many gastrointestinal disorders are often associated with vitamin D deficiency. These disorders frequently include impaired nutrient uptake, suppression of appetite, and difficulty gaining weight. Lastly, vitamin D may play a number of roles in immunity, with effects on tight junctions, pathogen invasion, commensal bacterial colonization, antimicrobe peptide secretion, and mucosal defense. For example, vitamin D administration may prevent influenza in some populations, as well as improve the cure rate of hepatitis C treatment, an infection characterized by loss of appetite and weight loss.

In yet another embodiment of the present invention, the method of present invention further comprises administering the mammal with zinc, ideally chelated zinc selected from group consisting of zinc gluconate, zinc picolinate, zinc orotate, zinc aspartate and zinc monomethionine. It is preferred that 10 to 150 mg of elemental zinc, ideally 20 to 40 mg is administered to the mammal per day. The purpose of adding zinc is to correct and prevent zinc deficiency, which is often characterized by reduced appetite and sense of taste, while avoiding excessive zinc supplementation, characterized by nausea and gastrointestinal upset, which may further reduce appetite and impair weight gain.

The nutritional supplement disclosed by the present invention also contains a number of different alkamide or isobutylamide compounds derived from different *Echinacea* species as illustrated above. These lipophilic alkamide or isobutylamide compounds are one of the primary classes of biologically active constituents in *Echinacea* that have been identified. The nutritional supplement can be in the form of a tablet, capsule, caplet, granule, particulate, agglomerate, spansule, chewable tablet, lozenge, or troche.

In one preferred embodiment of the present invention, the nutritional supplement comprises an antioxidant and at least two types of alkamide or isobutylamide compounds extracted or otherwise derived from *Echinacea* species selected from group consisting of *Echinacea angustifolia, Echinacea atrorubens, Echinacea laevigata, Echinacea pallida, Echinacea paradoxa, Echinacea purpurea, Echinacea sanguinea, Echinacea simulate* and *Echinacea tennesseensis*. Minerals such as zinc or magnesium can optionally be add to the nutritional supplement of the present invention to provide even better effect.

In one preferred embodiment of the present invention, the nutritional supplement is in solid dosage form and comprises Dodeca-2E,4E,8Z,10E/Z-tetraenoic acid isobutylamides extracted or otherwise derived from *Echinacea purpurea* and Dodeca-2E,4E-dienoic acid isobutylamide extracted or otherwise derived from *angustifolia*. While the ratio between these two is not critical, it is preferred that higher proportion of *Echinacea* extracts from *Echinacea angustifolia* is used when combining with *Echinacea* extracts derived from *Echinacea purpurea*. For example, the preferred proportion between *Echinacea angustifolia* and *Echinacea purpurea* is 6:4 to 8:2.

In another embodiment of the present invention, the nutritional supplement additionally includes other *Echinacea* alkamides selected from group consisting of Dodeca-2E,4Z-diene-8,10-diynoic acid isobutylamide; Undeca-2Z,4E-diene-8,10-diynoic acid isobutylamide; Undeca-2-ene-8,10-diynoic acid isobutylamide; Dodeca-2E-ene-8,10-diynoic acid 2-methylbutylamide; Dodeca-2E,4E,8Z-trienoic acid isobutylamide; Pentadeca-2E,9Z-diene-12,14-diynoic acid isobutylamide; and Dodeca-2E,4Z-diene-8,10-diynoic acid isobutylamide, or any combination thereof.

The antioxidant used is selected from group consisting of alpha tocopherol (vitamin E), butylated hydroxyanisole (BHA), butylated hydroxytoluene (BHT), ascorbyl palmitate, propyl gallate, dodecyl gallate, ethyl gallate, octyl gallate, lecithin, vitamin C, vitamin E or any combination thereof. Minerals such as magnesium and zinc can optionally be added to the nutritional supplement of the present invention.

In yet another preferred embodiment of the present invention, the Dodeca-2E,4E,8Z,10E/Z-tetraenoic acid isobutylamides has a minimal concentration of 0.03% by weight, on the dried basis, with ideal concentration between 0.05% to 0.20%. The Dodeca-2E,4E-dienoic acid isobutylamide has minimal concentration of 0.01% by weight, on the dried basis, with ideal concentration between 0.01% and 0.03%.

In yet another preferred embodiment of the present invention, when the *Echinacea* total alkamide concentration is less than 0.10% by weight, on the dried basis, it is recommended that the dosage of the *Echinacea* (as powder on a dry basis) is between 1600 to 3600 mg per day, ideally at 2400 mg per day. When *Echinacea* with a higher concentration is used, it is recommended that the dosage of the *Echinacea* (as powder on a dry basis) is between 400 to 1600 mg per day, ideally 800 to 1200 mg per day. It is also recommended that the nutritional supplement is taken daily with two to four dosages.

FIGS. 1 and 2 illustrate ideal formulations for the nutritional supplement of the present invention in capsules. Note that the present invention does not limit itself to the two examples illustrated below. Rather, these two examples merely demonstrate how the nutritional supplement can be formulated in accordance with the present invention. All the *Echinacea* extracts used in these two examples can be replaced with different type of *Echinacea* extracts disclosed in the present invention or commonly known to one skilled in the art. In addition, vitamins and minerals can also be replaced with ones that provide similar characteristics.

FIG. 3 is data collected from approximately 1200 test subjects showing their weight gain after taking formulation containing only *Echinacea* extracts. Table 2 is data collected from another 1200 test subjects showing their weight gain after taking formulation with *Echinacea* extracts, Vitamin D3, Zinc and Ternary Blend (as illustrated in FIG. 2). FIGS. 5 and 6 summarized the results of FIGS. 3 and 4.

As the results show in FIGS. 5 and 6, while both formulations provide effective weight gain for the individuals, formulation with Vitamin D3, Zinc and Ternary Blend provides approximately 26.4% higher rate of weight gain than formulation with only the *Echinacea* preparations.

Among other things, the present invention provides various benefits and advantages to the people seeking weight gain. Specifically, the present invention increases the appetite and slows the metabolism of an individual by activating the CB1 of the individual with *Echinacea* extracts, thereby enhancing the weight gain of the individual. First, the present invention is capable of temporarily slowing metabolic rate to hypometabolic levels for the purpose of increasing net calorie surplus for body weight gain. Second, the present invention is capable of treating conditions arising from hyperthyroidism. Third, with the novel antioxidant created from present invention's ternary blend, the present invention also provides a method for inhibiting the degradation and breakdown of alkamides from cut or ground plant stock, whether dry or wet, and extracts from *Echinacea*, whether obtained from alcohol or otherwise. This method further prevents oxidation from environmental exposure, including, but not limited to, oxygen and light.

It should be understood, of course, that the foregoing relates to exemplary embodiments of the invention and that modifications may be made without departing from the spirit and scope of the invention as set forth in the following claims.

What is claimed is:

1. A method of enhancing weight gain in a mammal in need thereof comprising administering a supplement comprising a daily dosage of 400 mg to 3600 mg of *Echinacea* powder comprising Dodeca-2E, 4E, 8Z,10E/Z-tetraenoic acid isobutylamides extracted or otherwise derived from *Echinacea* species selected from group consisting of *Echinacea angustifolia, Echinacea atrorubens, Echinacea laevigata, Echinacea pallida, Echinacea paradoxa, Echinacea purpurea, Echinacea sanguinea, Echinacea simulate* and *Echinacea tennesseensis* with a minimal concentration of 0.03% by weight of Dodeca-2E, 4E, 8Z,10E/Z-tetraenoic acid isobutylamides, and Dodeca-2E,4E-dienoic acid isobutylamide extracted or otherwise derived from *Echinacea* species selected from group consisting of *Echinacea angustifolia, Echinacea atrorubens, Echinacea laevigata, Echinacea pallida, Echinacea paradoxa, Echinacea purpurea, Echinacea sanguinea, Echinacea simulate* and *Echinacea tennesseensis* with a minimal concentration of 0.01% by weight of Dodeca-2E, 4E-dienoic acid isobutylamide;

at least three antioxidants comprising lecithin, vitamin C and vitamin E; and wherein the supplement is in the form of a tablet, capsule, caplet, granule, particulate, agglomerate, spansule, chewable tablet, lozenge or troche.

2. The method of claim 1, wherein the Dodeca-2E,4E,8Z,10E/Z-tetraenoic acid isobutylamides is extracted or otherwise derived from *Echinacea* purpurea or *Echinacea angustifolia*.

3. The method of claim 1 further comprises:
administering an effective amount of zinc or magnesium.

4. The method of claim 1, wherein concentration of the Dodeca-2E,4E,8Z,10E/Z-tetraenoic acid isobutylamides is between 0.03% to 0.20% and concentration of the Dodeca-2E, 4E-dienoic acid isobutylamide is between 0.01% to 0.03%.

5. The method of claim 1 further comprises administering an effective amount of Dodeca-2E-ene-8,10-diynoic acid 2-methylbutylamide and Pentadeca-2E,9Z-diene-12,14-diynoic acid isobutylamide extracted or otherwise derived from *Echinacea angustifolia*.

6. A nutritional supplement that causes weight gain in a mammal in need thereof, the supplement comprising:

a daily dosage of 400 mg to 3600 mg of *Echinacea* powder comprising Dodeca-2E,4E,8Z,10E/Z-tetraenoic acid isobutylamides extracted or otherwise derived from *Echinacea* species selected from group consisting of *Echinacea angustifolia, Echinacea* atrorubens, *Echinacea laevigata, Echinacea pallida, Echinacea paradoxa, Echinacea* purpurea, *Echinacea sanguinea, Echinacea simulate* and *Echinacea tennesseensis* with a minimal concentration of 0.03% by weight of Dodeca-2E, 4E,8Z, 10E/Z-tetraenoic acid isobutylamides; and Dodeca-2E,4E-dienoic acid isobutylamide extracted or otherwise derived from *Echinacea* species selected from group consisting of *Echinacea angustifolia, Echinacea* atrorubens, *Echinacea laevigata, Echinacea pallida, Echinacea paradoxa, Echinacea* purpurea, *Echinacea sanguinea, Echinacea simulate* and *Echinacea tennesseensis* with a minimal concentration of 0.01% by weight of Dodeca-2E, 4E-dienoic acid isobutylamide;

at least three antioxidants comprising lecithin, vitamin C and vitamin E; and wherein the supplement is in the form of a tablet, capsule, caplet, granule, particulate, agglomerate, spansule, chewable tablet, lozenge or troche.

7. The nutritional supplement of claim 6 further comprises vitamin D3.

8. The nutritional supplement of claim 6, wherein the Dodeca-2E,4E,8Z,10E/Z-tetraenoic acid isobutylamides is extracted or otherwise derived from *Echinacea* purpurea and the Dodeca-2E, 4E-dienoic acid isobutylamide is extracted or otherwise derived from *Echinacea angustifolia*.

9. The nutritional supplement of claim 6, wherein proportion of the *Echinacea angustifolia* alkamides is higher than the proportion of the *Echinacea* purpurea alkamides.

10. The nutritional supplement of claim 7, wherein the Dodeca-2E,4E,8Z,10E/Z-tetraenoic acid isobutylamides has concentration between 0.03% to 0.20% and the Dodeca-2E, 4E-dienoic acid isobutylamide has concentration between 0.01% to 0.03%.

* * * * *